(12) United States Patent
Hall

(10) Patent No.: US 10,555,863 B2
(45) Date of Patent: Feb. 11, 2020

(54) CRYOTHERAPY COMPRESSION SYSTEM

(71) Applicant: Jacob Randy Hall, Draper, UT (US)

(72) Inventor: Jacob Randy Hall, Draper, UT (US)

(73) Assignee: Jacob Randy Hall, Midway, UT (US)

( * ) Notice: Subject to any disclaimer, the term of this patent is extended or adjusted under 35 U.S.C. 154(b) by 755 days.

(21) Appl. No.: 14/207,225

(22) Filed: Mar. 12, 2014

(65) Prior Publication Data

US 2014/0276258 A1    Sep. 18, 2014

Related U.S. Application Data

(60) Provisional application No. 61/786,354, filed on Mar. 15, 2013.

(51) Int. Cl.
| | |
|---|---|
| *A61H 11/00* | (2006.01) |
| *A61H 1/00* | (2006.01) |
| *A61F 7/02* | (2006.01) |
| *A61F 7/00* | (2006.01) |

(52) U.S. Cl.
CPC ............. *A61H 1/008* (2013.01); *A61H 11/00* (2013.01); *A61F 7/00* (2013.01); *A61F 7/02* (2013.01)

(58) Field of Classification Search
CPC .. A61H 11/00; A61H 11/02; A61H 2011/005; A61H 15/02; A61H 2201/02; A61H 2201/0207; A61H 2201/0214; A61H 2201/0221; A61H 2201/0242; A61H 2201/165; A61H 2201/1654; A61F 7/02; A61F 2007/0225; A61F 2007/0228; A61F 2007/023; A61F 2007/0231; A61F 2007/0233; A61F 2007/0234; A61F 2007/0236; A61F 2007/0238

See application file for complete search history.

(56) References Cited

U.S. PATENT DOCUMENTS

| | | | | |
|---|---|---|---|---|
| 1,567,931 A | * | 12/1925 | Epler ........................ | A61F 7/02 607/112 |
| 2,573,791 A | * | 11/1951 | Howells .................... | A61F 7/03 602/14 |
| 2,699,165 A | * | 1/1955 | Ferrier ................. | A61H 9/0078 128/DIG. 20 |
| 4,556,055 A | * | 12/1985 | Bonner, Jr. ............... | A61F 7/10 128/DIG. 15 |
| 4,676,247 A | * | 6/1987 | Van Cleve ................ | A61F 7/02 607/112 |

(Continued)

FOREIGN PATENT DOCUMENTS

WO  PCT/US2014/026462    7/2014

*Primary Examiner* — Michael J Tsai
(74) *Attorney, Agent, or Firm* — Workman Nydegger

(57) ABSTRACT

In one example, a therapy system is provided that includes an inner layer and an outer layer including first and second portions and disposed outside of the inner layer. A therapeutic device, such as a cold pack for example, is provided that is configured to be positioned inside the inner layer. The therapy system also includes an adjustable tightening mechanism connected to the first and second portions of the outer layer and operable to change a position of one of the first and second portions relative to the other of the first and second portions so as to adjust a magnitude of a compressive force exerted by the outer layer on an extremity of a user when the extremity is positioned within an opening defined by the inner layer.

13 Claims, 23 Drawing Sheets

(56) References Cited

U.S. PATENT DOCUMENTS

| | | | |
|---|---|---|---|
| 5,179,942 A * | 1/1993 | Drulias | A61F 5/028 128/101.1 |
| 5,346,461 A * | 9/1994 | Heinz | A61F 5/028 128/121.1 |
| 5,470,353 A * | 11/1995 | Jensen | A61F 7/0097 607/104 |
| 5,697,962 A * | 12/1997 | Brink | A61F 7/02 126/204 |
| 5,716,335 A | 2/1998 | Iglesias | |
| 5,741,220 A * | 4/1998 | Brink | A61F 5/0125 602/14 |
| 6,149,617 A | 11/2000 | McNally | |
| 7,727,172 B2 * | 6/2010 | Wang | A61F 5/028 602/19 |
| 8,460,352 B2 * | 6/2013 | DeMore | A61F 7/02 607/108 |
| 2002/0068890 A1 * | 6/2002 | Schwenn | A61F 5/0193 602/19 |
| 2004/0168459 A1 | 9/2004 | Blackstone | |
| 2004/0186539 A1 * | 9/2004 | Nozik | A61F 13/66 607/108 |
| 2006/0149178 A1 | 7/2006 | Dunfee | |
| 2006/0191063 A1 | 8/2006 | Elkins | |
| 2009/0112136 A1 * | 4/2009 | Litton | A61H 11/00 601/48 |
| 2011/0098792 A1 * | 4/2011 | Lowe | A61F 7/02 607/104 |
| 2012/0029404 A1 * | 2/2012 | Weaver, II | A61F 5/0111 602/27 |
| 2012/0143295 A1 * | 6/2012 | Moore | A61F 7/007 607/112 |
| 2013/0345612 A1 * | 12/2013 | Bannister | A61B 5/1116 602/19 |
| 2014/0135672 A1 * | 5/2014 | Joseph | A61F 5/028 602/19 |

\* cited by examiner

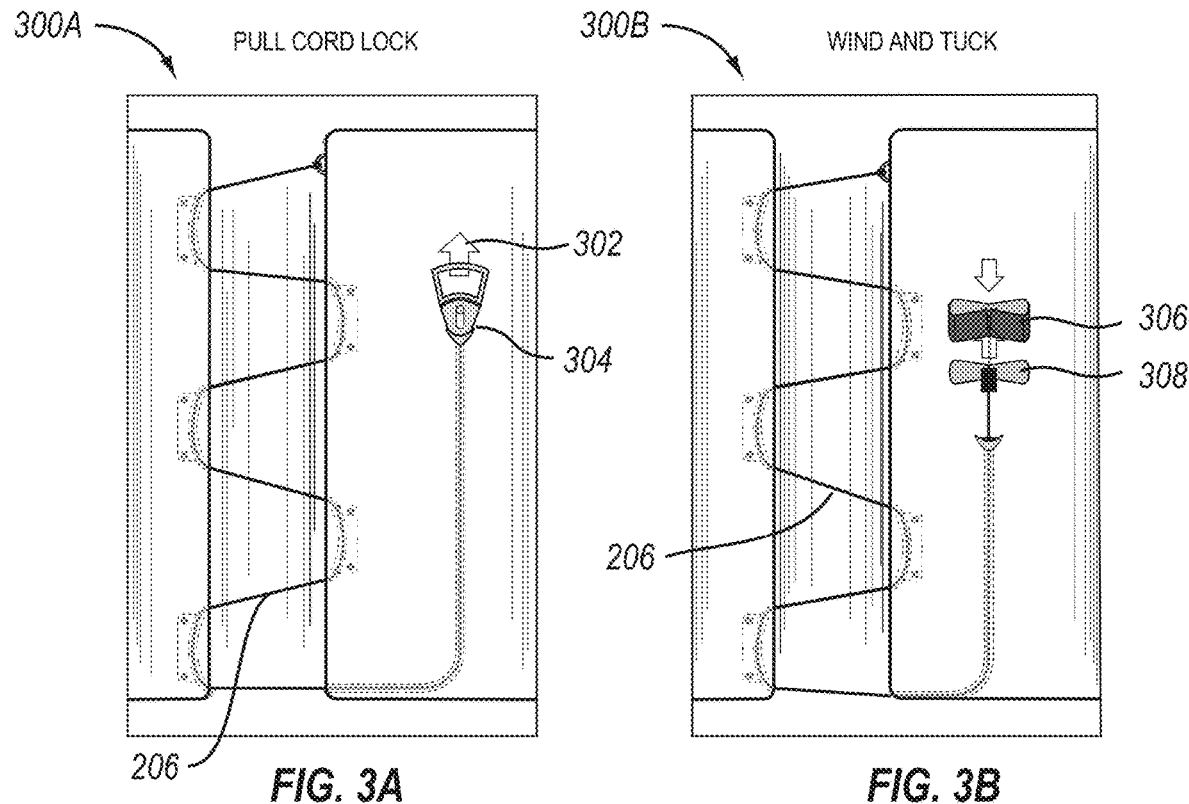
FIG. 3A
FIG. 3B
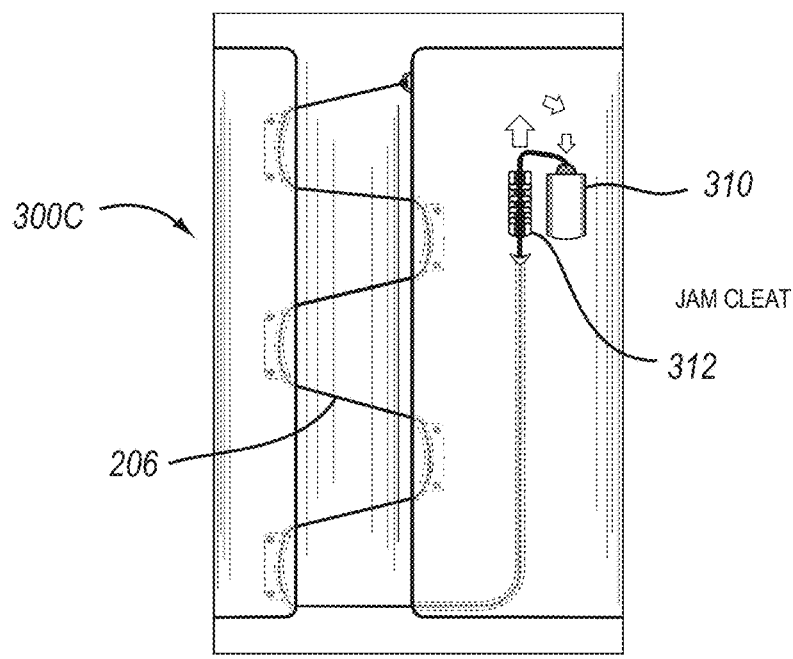
FIG. 3C

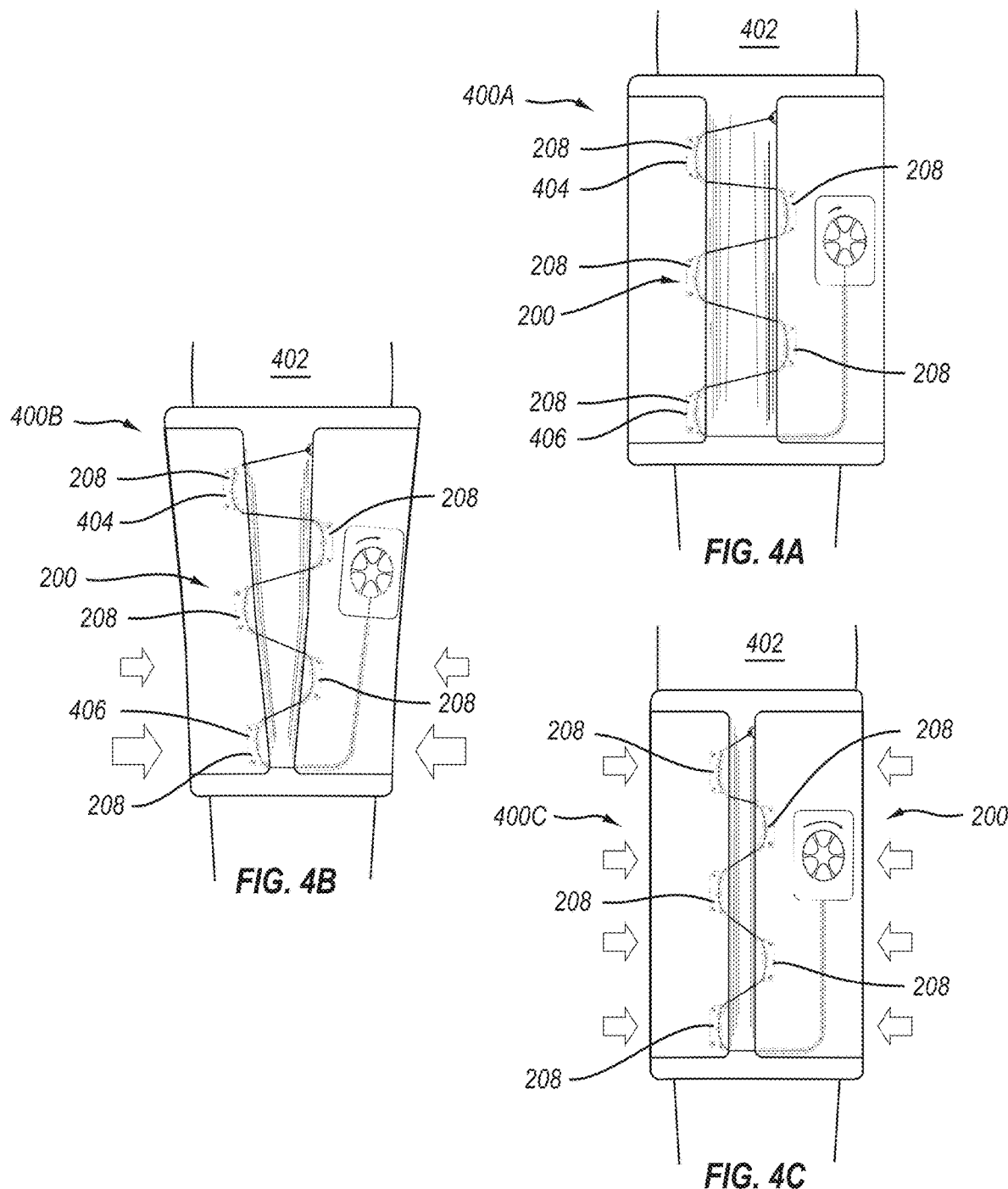

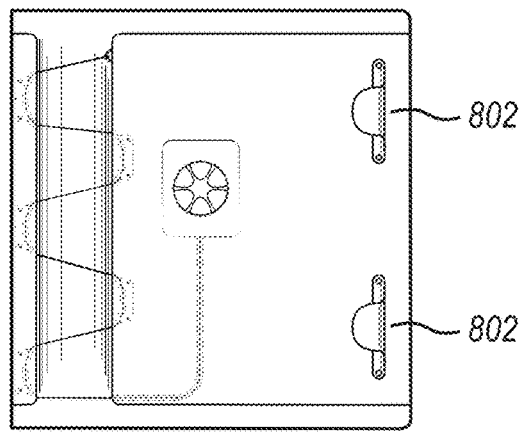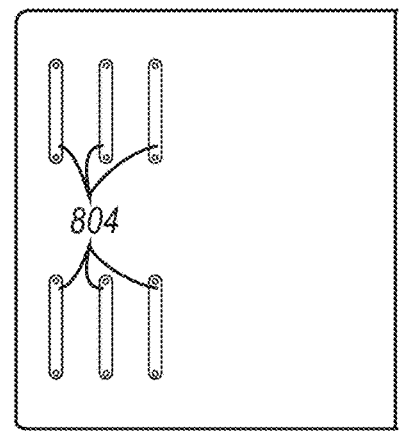
FIG. 8A
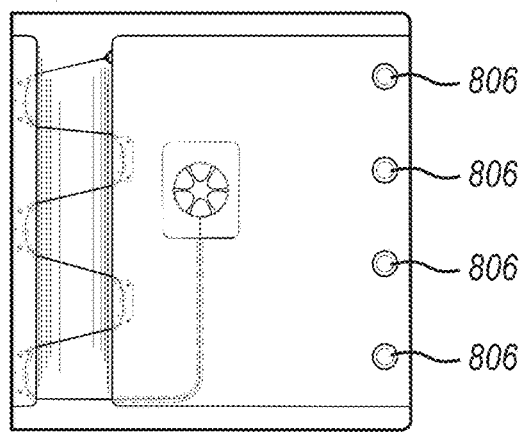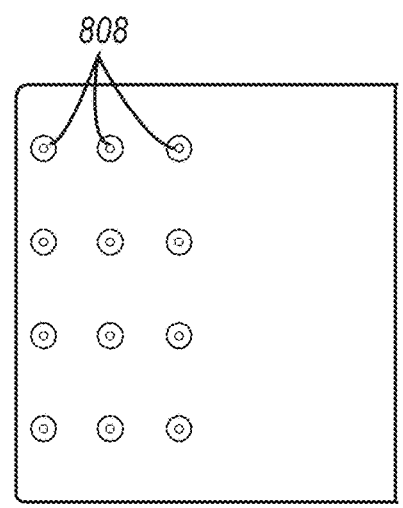
FIG. 8B
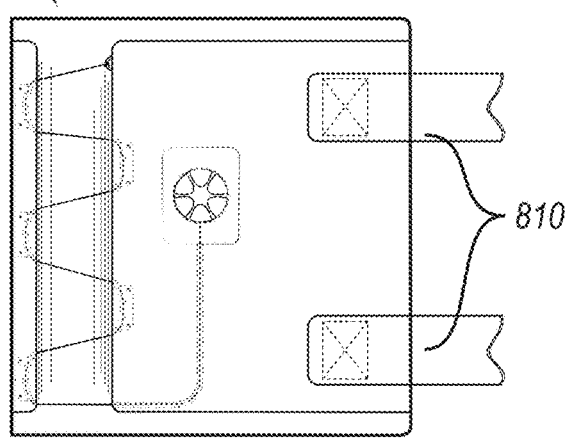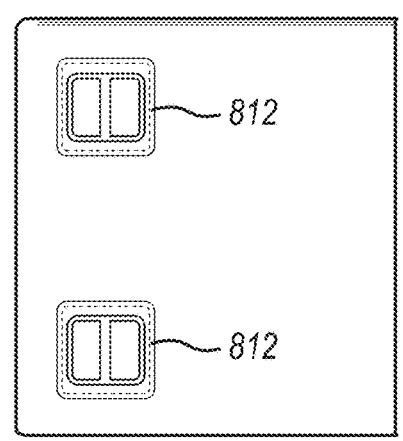
FIG. 8C

CRYOTHERAPY COMPRESSION SYSTEM

RELATED APPLICATION

This application hereby claims priority to U.S. Provisional Patent Application Ser. No. 61/786,354, entitled CRYOTHERAPY COMPRESSION SYSTEM, filed Mar. 15, 2013, and incorporated herein in its entirety by this reference.

FIELD OF THE INVENTION

The embodiments discussed herein are related to cryotherapy.

BACKGROUND

Cold compression therapy is used in sports medicine and injury rehabilitation. More particularly, cold compression therapy may be used for injuries related to soft tissue trauma such as post-surgical rehabilitation, sports injuries, or arthritic conditions, for instance.

Cold compression therapy is a combination of cryotherapy and compression therapy. Cryotherapy generally includes treatment of an injury through direct application of cold temperatures to the injured area. By applying the cold temperatures, heat is transferred away from the injured area, which causes vasoconstriction and reflexive vasodilation, which decreases metabolism and may alleviate minor pain. Cryotherapy systems include a wide range of devices from a bag of ice to cryo-saunas in which a user can enter and sit for some time to treat an entire body of the user.

Compression therapy generally refers to exerting an external pressure on an injured area. The external pressure acts on the tissue to decrease or prevent swelling. Like cryotherapy systems, compression systems include a wide range of devices from stretchy socks to wraps with complex geometric design having hook and loop systems for securing the wraps to the injured area.

Most existing cold compression therapy systems combine application of cold temperatures with application of external pressure. Some of the cold compression systems are static. Users of static cold compression systems cannot adjust or quickly alleviate the external pressure exerted on the injured area. These static cold compression systems are not intended to be adjusted and often require substantial re-positioning and modifications to various straps to change the external pressure.

Alternatively, some cold compression systems are dynamic. Dynamic cold compression systems allow adjustment of the external pressure. However, dynamic adjustment systems often require large-scale compressors with complex controls to allow a user to control the external pressure applied to the injured area. These systems are large, expensive, and cumbersome to operate. The majority of dynamic cold compression systems are not practical for individual use due to the expense and difficulty involved in proper use. Thus, these cold compression systems are used by physical therapists.

The subject matter claimed herein is not limited to embodiments that solve any disadvantages or that operate only in environments such as those described above. Rather, this background is only provided to illustrate one example technology area where some embodiments described herein may be practiced.

BRIEF SUMMARY OF SOME ASPECTS OF THE DISCLOSURE

It should be noted that the embodiments disclosed herein do not constitute an exhaustive summary of all possible embodiments, nor does this brief summary constitute an exhaustive list of all aspects of any particular embodiment(s). Rather, this brief summary simply presents selected aspects of some example embodiments. It should be noted that nothing herein should be construed as constituting an essential or indispensable element of any invention or embodiment. Rather, various aspects of the disclosed embodiments may be combined in a variety of ways so as to define yet further embodiments. Such further embodiments are considered as being within the scope of this disclosure. As well, none of the embodiments embraced within the scope of this disclosure should be construed as resolving, or being limited to the resolution of, any particular problem(s). Nor should such embodiments be construed to implement, or be limited to implementation of, any particular technical effect(s) or solution(s).

Disclosed embodiments are generally concerned with a therapy system that enables a user to apply a thermal pack, such as a cold pack or a heat pack, or other therapeutic element, such as a TENS device, to an affected area while, also enabling the user to apply and maintain an external pressure to the affected area. The applied external pressure may be adjusted by the user. Embodiments within the scope of this disclosure may include any one or more of the following elements, and features of elements, in any combination: a layer having first and second ends and configured to be wrapped around a portion of the anatomy of a user; a sleeve configured to removable receive a portion of the anatomy of a user; a cold pack; a therapeutic element, which may take the form of any of a heat pack, cold pack, TENS device, or water circulation pad; a layer having first and second ends and configured to be wrapped around a portion of the anatomy of a user, and the layer includes an elastic portion; a sleeve configured to removably receive a portion of the anatomy of a user, and the sleeve may optionally include an elastic portion; one or more cold packs; one or more heat packs; a cold compress; a cold water circulation system including a water circulation pad; an adjustable tightening mechanism operable by a user to vary an external pressure exerted by a layer or sleeve on a portion of the anatomy of the user; a securing mechanism; an adjustable tightening mechanism that includes a lace and one or more lace retainers, and the tension in the lace is adjustable by a user; an adjustable tightening mechanism that includes a lace and one or more lace retainers, and the tension in the lace is adjustable by a user using a rotate-and-lock mechanism of the adjustable tightening mechanism; an inner layer; an outer layer; a compressible pad shaped to conform with a portion of the anatomy of a user; a compressible pad having a first portion that is thicker than a second portion of the compressible pad; a transcutaneous electrical nerve stimulation (TENS) unit including one or more pads, one or more of which may be removable from a sleeve or layer; a cryotherapy system configured to fit one or more of, an ankle-foot combination of a user, a shoulder of a user, a wrist of a user, an elbow of a user, a calf of a user, a hip of a user; a foot-to-hip of a user; and, an ankle-to-hip of a user; a self-contained cryotherapy system that requires no external water supply or power supply; and, a cryotherapy system that includes a plurality of tightening mechanisms.

Following is a non-exclusive list of embodiments within the scope of the invention. It should be understood that aspects of the various embodiments disclosed herein may be combined in other ways to define still further embodiments.

1. A system comprising: an inner layer, the inner layer being continuous between a first end and a second end of the cryotherapy system and configured such that the inner layer can be configured to define an opening through which an extremity of a user may be introduced; an outer layer attached to the inner layer, the outer layer including a first portion of the outer layer and a second portion of the outer layer; a cold pack positioned between the inner layer and the outer layer; and a tightening mechanism configured to move the first portion of the outer layer towards the second portion of the outer layer and to maintain the first portion with respect to the second portion, thereby pressing the cold pack against the inner layer and applying therapeutic compression to the extremity.

2. The system of embodiment 1, wherein the tightening mechanism is configured to move the first portion of the outer layer towards the second portion of the outer layer and to maintain the first portion with respect to the second portion.

3. The system of embodiment 1, further comprising a foam pad, the foam pad including at least two thickness such that a first pressure is applied at a first area and a second pressure is applied at a second area.

4. The system of embodiment 1, further comprising a foam pad positioned between the outer layer and the cold compress, the foam pad including at least two thickness such that a first pressure is applied at a first area and a second pressure is applied at a second area when the outer layer is moved towards the second portion of the outer layer.

5. The systems of either of embodiments 3 or 4, wherein the at least two thickness are further positioned such that the first pressure is applied to a low point of a joint on the extremity and the second pressure is applied to a high point of the joint on the extremity.

6. The systems of any of embodiments 1-5, wherein the tightening mechanism includes: a lace; a first lace retainer secured on the first portion, the lace routed through the first lace retainer; a second lace retainer secured on the second portion, the lace routed through the second lace retainer; and a lace tensioner configured to apply tension to the lace and to retract the lace, which moves the first lace retainer towards the second lace retainer.

7. The system of embodiment 6, further comprising: a lace conduit positioned within the second portion of the outer layer and coupled to the lace tensioner, the lace conduit configured such that the lace exits the lace conduit and enters the first lace retainer.

8. The system of embodiment 7, wherein the lace exits the lace conduit at a substantially right angle to an edge of the first portion.

9. The system of embodiment 1, wherein the tightening mechanism includes: a lace; a first plurality of lace retainers secured on the first portion, the lace routed through each of the first plurality of lace retainer; a second plurality of lace retainers secured on the second portion, the lace routed through each of the second plurality of lace retainers; and a lace tensioner configured to apply tension to the lace and to retract the lace which moves the first lace retainer towards the second lace retainer.

10. The system of embodiment 9, wherein each of the first plurality of lace retainers and each of the second plurality of lace retainers are U shaped and include an inlet and an outlet oriented substantially perpendicular to an edge of the first portion and a length oriented substantially parallel to the edge of the first portion.

11. The system of embodiments 9 or 10, wherein the first plurality of lace retainers are staggered with respect to the second plurality of lace retainers, such that a first inlet of a first lace retainer of the first plurality of lace retainers is positioned across from an outlet of a lace conduit; and a first outlet of the first lace retainer is positioned across from second inlet of a second lace retainer of the second plurality of lace retainers.

12. The system of any of embodiments 9-11, wherein: the first plurality of lace retainers and the second plurality of lace retainers include a proximate lace retainer positioned nearest a core of a user; the first plurality of lace retainers and the second plurality of lace retainers include a distal lace retainer positioned farthest from the core of the user; and when the tightening mechanism moves the first portion of the outer layer towards the second portion of the outer layer, the distal lace retainers move together before the proximate lace retainer.

13. The system of any of embodiments 9-12, wherein: each of the first plurality of lace retainers is separated from adjacent lace retainers of the first plurality of lace retainers by a constant distance; and each of the second plurality of lace retainers is separated from adjacent lace retainers of the second plurality of lace retainers by the constant distance.

14. The system of any of embodiments 9-12, wherein: one of the first plurality of lace retainers is separated from an adjacent lace retainers of the first plurality of lace retainers by a first distance; and a second of the first plurality of lace retainers is separated from a second adjacent lace retainer of the first plurality of lace retainers by a second distance.

15. The system of any of embodiments 9-12, wherein: one of the second plurality of lace retainers is separated from an adjacent lace retainers of the second plurality of lace retainers by a first distance; and a second of the second plurality of lace retainers is separated from a second adjacent lace retainer of the second plurality of lace retainers by a second distance.

16. A system comprising: a layer of material configured to at least partially surround an extremity of a user, the layer having a first state in which the layer of material is secured to the extremity and applies a first external pressure to the extremity, and a second state in which a second external pressure is applied to the extremity; and a tightening mechanism configured to transition the layer from the first state to the second state.

17. The system of embodiment 16, further comprising: a second layer of material, the second layer of material configured such that when the layer is secured to the user a separation exists between a first portion of the second layer and a second portion of the second layer.

18. The system of embodiments 16 or 17, wherein the layer is continuous without a separation.

19. A system comprising: a plurality of layers configured to be applied to in a first arrangement and a second arrangement to an extremity of a user, the first arrangement including the extremity being introduced into an opening defined when at least one of the plurality of layers is secured to the user and a separation in another of the plurality of layers has a first dimension, and the second arrangement including the other layer in tension such that the separation in the other layer has a reduced dimension, which constricts at least one dimension of the opening.

20. The system of any of embodiments 16-19, further comprising a cold compress.

21. The system of embodiments 1 or 20, wherein the cold pack includes a cold therapy water circulation system.

22. The system of any of embodiments 20-21, wherein the cold pack is removable.

23. The system of embodiment 1, wherein the cold pack is sewn into the inner layer.

24. The system of any of embodiments 1-22, wherein the system is configured to fit a wrist, a knee, a shoulder, a hip, an ankle-foot combination, a calf, an elbow, a foot-to-hip of a user; or, an ankle-to-hip of a user of a user.

25. The system of any of embodiments 1-24, wherein the tightening mechanism includes: a pull-and-lock mechanism; a wind and tuck mechanism; a jam cleat; or a rotate-and-lock mechanism.

26. The system of any of embodiments 1-25, further comprising a securing mechanism configured to secure the cryotherapy system to the user and to form the opening.

27. The system of embodiment 26, wherein the securing mechanism includes a set of buttons, a set of snaps, a belt tightening system, metal hooks, or a hoop and loop system.

28. The system of embodiment 16, wherein the layer of material comprises a cold pack and the tightening mechanism being attached directly to the cold compress.

29. The system of embodiment 16, further comprising a transcutaneous electrical nerve stimulation (TENS) unit.

30. The system of embodiment 16, wherein the tightening mechanism is operated through a manual act of a user.

31. A method of cryotherapy comprising: introducing an extremity into an opening defined by a layer of material; securing the layer of material to the extremity such that a first pressure is applied to an injured area; and operating a tightening mechanism such that a second pressure is applied to the injured area.

BRIEF DESCRIPTION OF THE DRAWINGS

Example embodiments will be described and explained with additional specificity and detail through the use of the accompanying drawings in which:

FIGS. 3A-3C illustrate example lace tensioners that may be implemented in the tightening mechanism of FIG. 2;

FIGS. 4A-4C illustrate an example sequential tightening process that may be implemented by the tightening mechanism of FIG. 2;

FIGS. 8A-8C illustrate example securing mechanisms that may be implemented in the cryotherapy system of FIGS. 1A-1D;

DETAILED DESCRIPTION OF EXAMPLE EMBODIMENTS

Figure 1A:
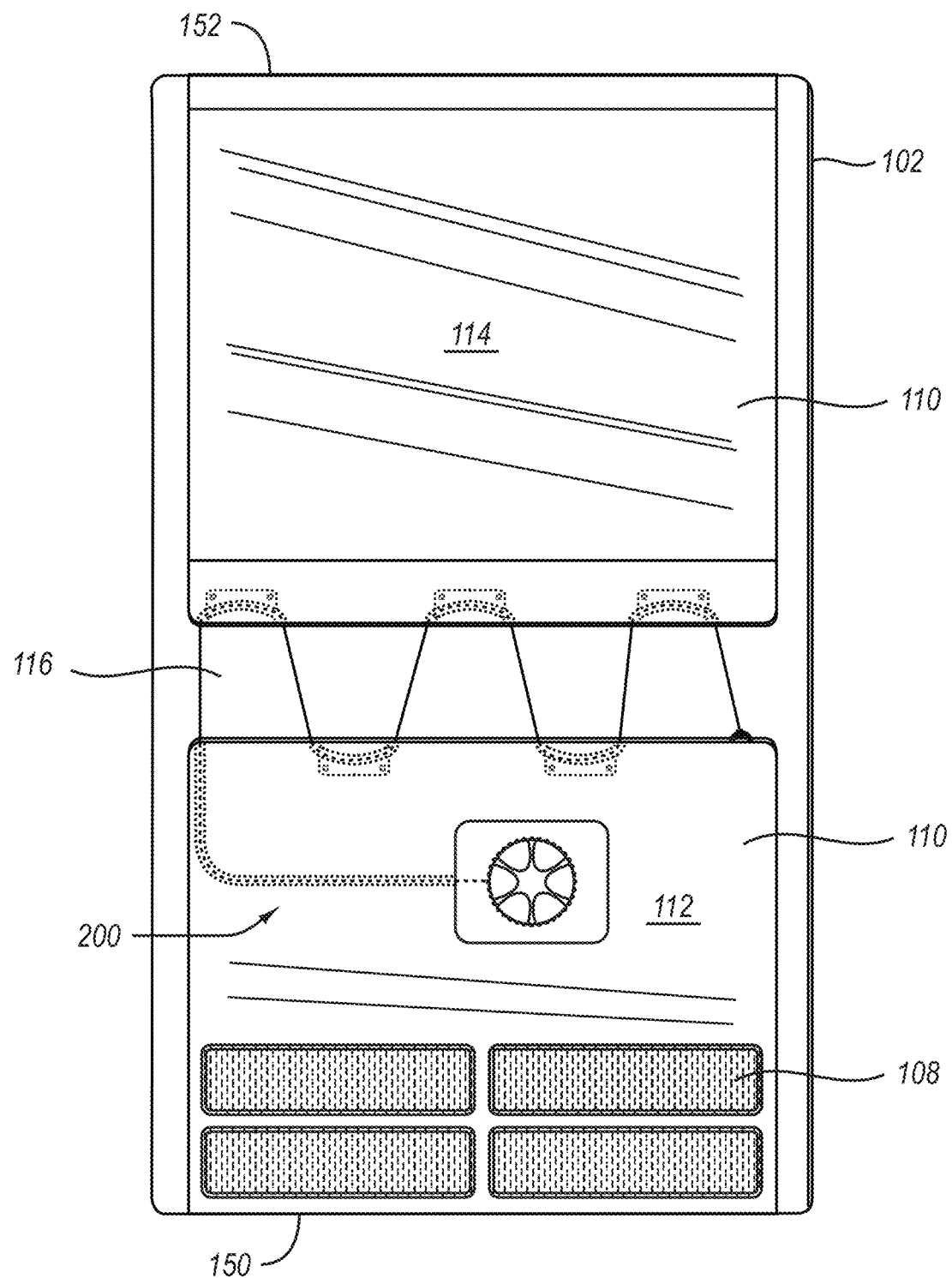
FIGS. 1A-1D illustrate an example cryotherapy system.

Some example embodiments of the present invention will be explained with reference to the accompanying drawings. In general, such embodiments can be used in a variety of applications, though it should be noted that the following examples are not intended to limit the scope of the invention in any way. For example, embodiments of the invention can be used to treat an injury that a user has sustained. This treatment may occur near in time to the injury and/or over a period of time after the injury has been sustained. Embodiments of the invention are not limited to use in treating injuries however. For example, embodiments of the invention can be used to aid in the recovery of a user after endurance events that may extend over a relatively long period of time, such as from several hours to several days.

It should be noted that while various embodiments disclosed herein are referred to as constituting a cryotherapy system, at least some of such embodiments can be configured and used to provide only compression, without any thermal therapy component or device. By way of illustration, an embodiment that includes a removable therapeutic device, such as a cold pack for example, can be used without the cold pack to provide only compression therapy.

As well, embodiments of the invention can be used in other than therapeutic applications. For example, embodiments can be used as, or together with, a splint to stabilize a body part, such as a limb, suspected to be broken, or that has undergone some other traumatic type of injury. The splint, or splints, can be rigid or semi-rigid elements of metal, wood, plastic and/or any other suitable material(s) that are separate from one of the disclosed devices, or can be incorporated into one or more layers of those devices. The splints may or may not be removable from such layer(s).

As another example, embodiments of the invention can be sized and configured so as to take the form of a tourniquet. The variable compression afforded by the aforementioned embodiments is well suited to these applications, among others, and such embodiments can be included as an element of trauma kits and other collections of medical equipment for emergency, and other, use.

Moreover, while some of the disclosed embodiments are suited for use with humans, other embodiments can be used for treatment of animals. Thus, the scope of the invention is not limited to devices that are configured to fit the human anatomy only, but extends as well to devices configured to fit the anatomy of various types and sizes of animals.

With regard to the various layers and sleeves disclosed herein, it should be noted that the layers and sleeves can have any shape or size. Moreover, any of the layers and sleeves disclosed herein may include an elastic portion, or may substantially comprise an elastic material. As well, any of the layers and sleeves may include a portion made of absorbent material, or may substantially comprise an absorbent material, that can absorb any moisture that may condense on or near a cold pack. Further, any of the layers and sleeves disclosed herein may include any one or more of an elastic material, a waterproof or water-resistant material, and an absorbent material. Further, various materials can be used in the construction of embodiments of the invention, and such materials include, but are not limited to, nylon, plastic, polyester, PTFE, rubber, cotton, metal, fiberglass, carbon fiber, composites, and any group of one or more of the foregoing. Finally, one or more layers or sleeves of any embodiment within the scope of this disclosure may include thermal insulation.

Figure 1B:
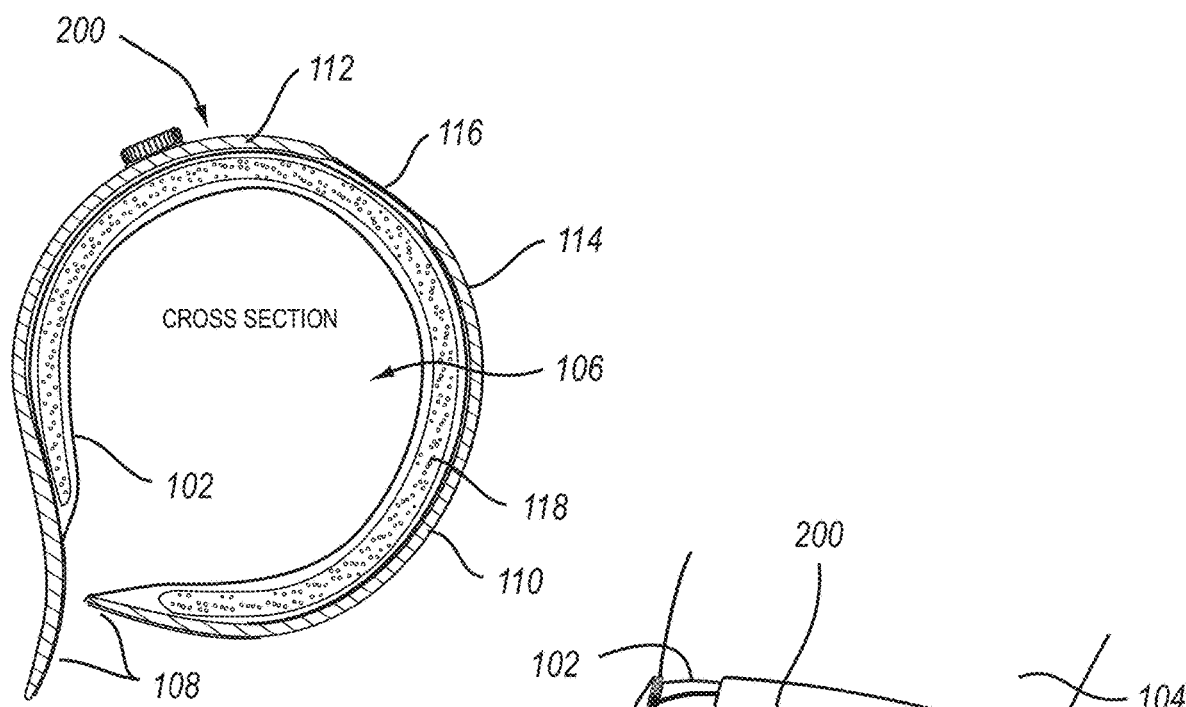
Figure 1C:
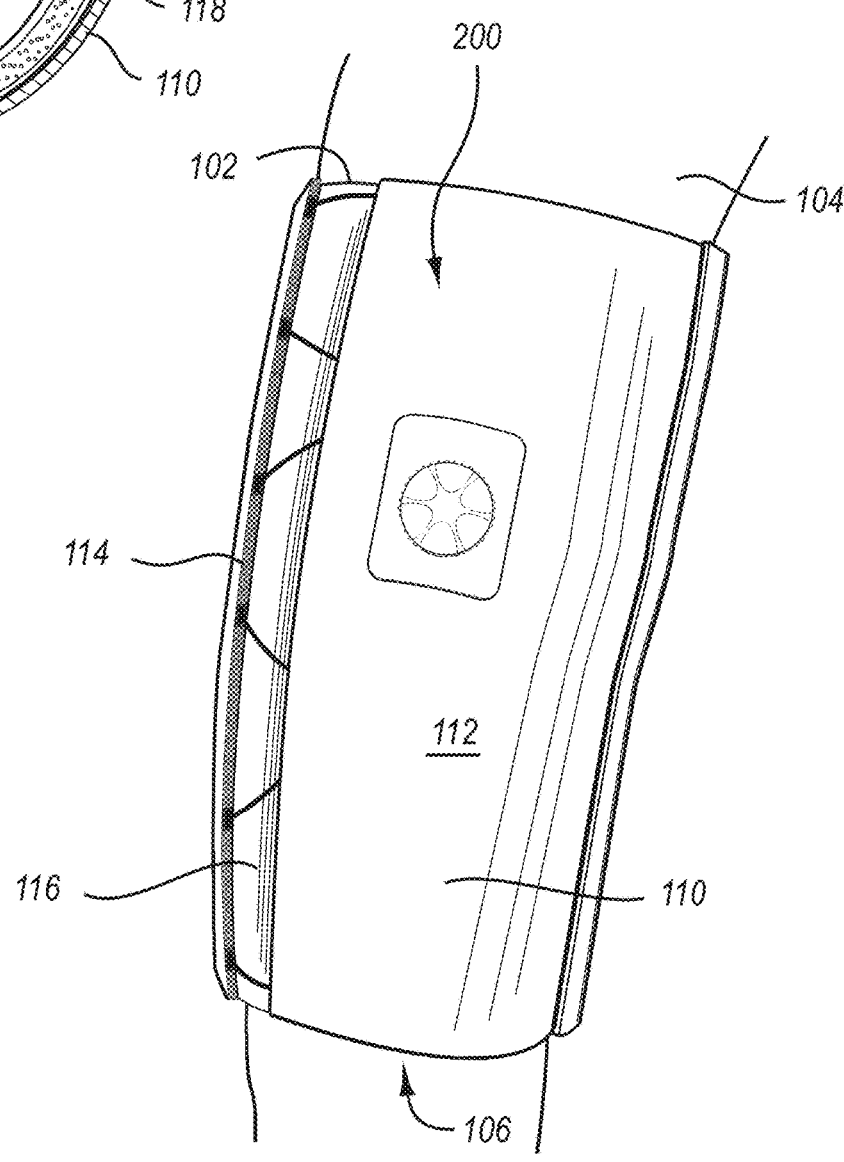
Figure 1D:
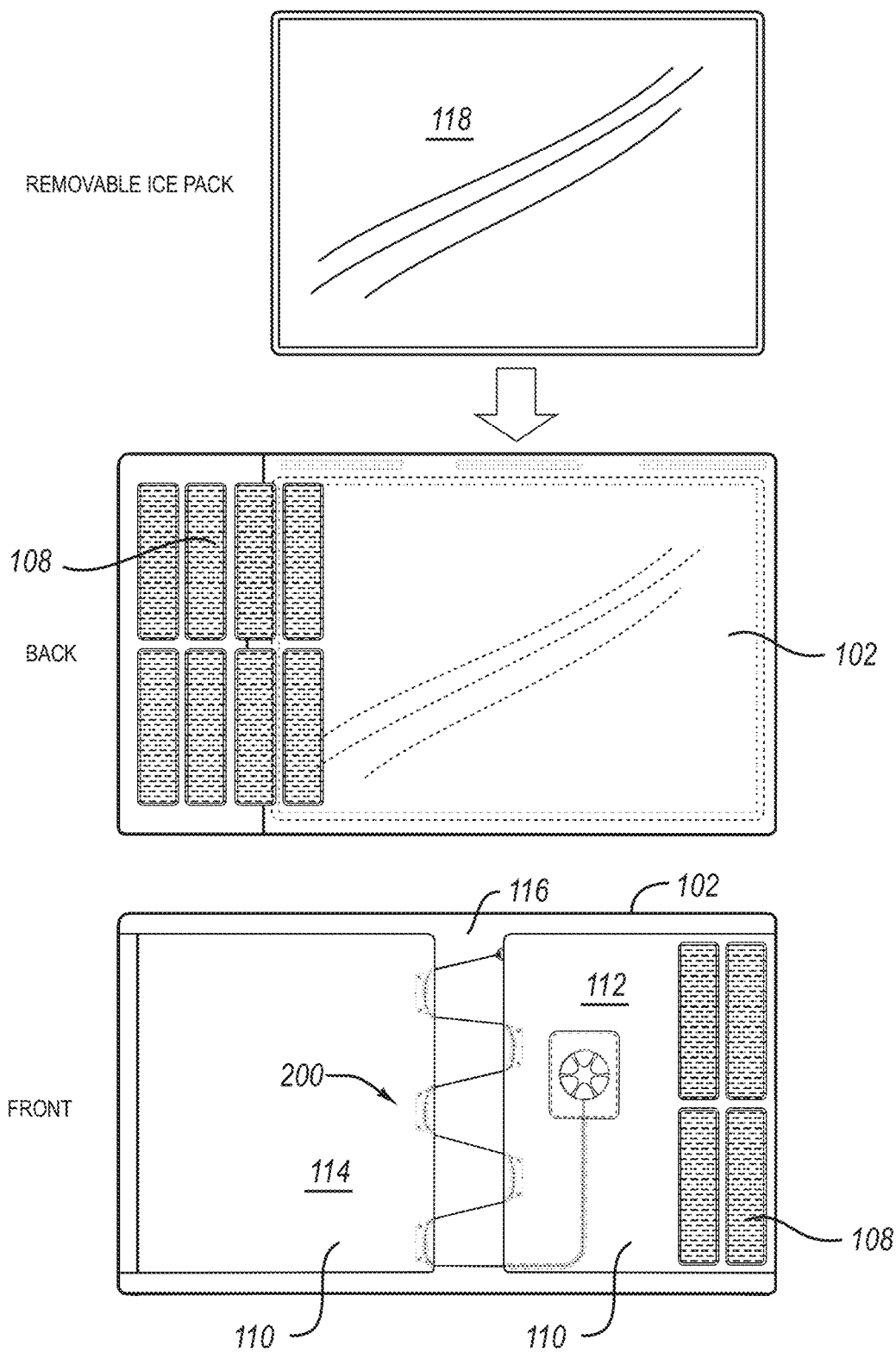

FIGS. 1A-1D illustrate an example cryotherapy system 100 according to some embodiments described herein. Specifically, FIG. 1A is an external view of the cryotherapy system 100 apart from a user and unwrapped. FIG. 1B is a sectional view of the cryotherapy system 100 in a wrapped, but unsecured configuration. FIG. 1C is the cryotherapy system 100 worn by a user 104 (FIG. 1C only). FIG. 1D is the cryotherapy system 100 exploded into some individual components. It should be appreciated that a detailed description of the cryotherapy system 100 is provided herein, however this description and principles thereof may be applicable to other embodiments, which may include some dissimilar and/or some additional features.

Generally, the cryotherapy system 100 enables a user to apply a cold pack while further applying and maintaining an adjustable external pressure to an injured area. The adjustable external pressure may be controlled manually by the user 104. In some embodiments, the cryotherapy system 100 may be self-contained. Thus, in these and other embodiments, one or more external systems such as external electrical systems, water-cooling systems, and/or water circulation systems may be unnecessary. The manual control may simplify the cryotherapy system 100 and reduce the expense and training required to operate the cryotherapy system 100.

With reference to FIGS. 1A-1D, the cryotherapy system 100 may include an inner layer 102. The inner layer 102 is a continuous layer extending from a first end 150 to a second end 152 (FIG. 1A only). Additionally the inner layer 102 may be configured to be placed adjacent to the user 104. For example, the inner layer 102 may be placed directly on skin of the user 104 or the user 104 may place a towel between the skin of the user 104 and the inner layer 102. The inner layer 102 depicted in FIGS. 1A-1D is substantially rectangular. However, this is not meant to be limiting. The general shape of the inner layer 102 may take an anatomical shape. For instances, some embodiments of the cryotherapy system 100 may be configured to be worn during some activity. Accordingly, these embodiments may be configured with one or more sections removed to allow for such activity.

With continued reference now to the particular example of FIGS. 1A-1D, the inner layer 102 is configured such that when secured to the user 104, the inner layer 102 defines an opening 106 (FIGS. 1B and 1C only). The opening 106 is configured such that an extremity of the user 104 may be introduced into the opening 106. In some embodiments, introduction of the extremity into the opening 106 may occur while the inner layer 102 is being secured to the user 104. With the extremity of the user 104 introduced into the opening 106, the cryotherapy system 100 is positioned around an injured area of the user 104. In this configuration, the user 104 can generally position the cryotherapy system 100 on the injured area or adjust the position of the cryotherapy system 100 to increase comfort. For example, in FIG. 1C, a leg of the user 104 is introduced into the opening 106. In this configuration, the user 104 may position the cryotherapy system 100 such that the cryotherapy system 100 is fit around the knee of the user 104.

The opening 106 may be substantially cylindrical, as depicted in FIGS. 1A-1D, or may take a more complex shape. Some additional examples of the opening 106 with more complex shapes are provided with reference to FIGS. 14-19B.

The cryotherapy system 100 may include a securing mechanism 108. The securing mechanism may be used to define the opening 106 and to secure the cryotherapy system 100 to the user 104. The securing mechanism 108 depicted in FIGS. 1A-1D is a hook and loop system. However, this is not meant to be limiting.

Referring to FIGS. 8A-8C, some example securing mechanisms that may be implemented in the cryotherapy system 100 of FIGS. 1A-1D are illustrated. In each of FIGS. 8A-8C, two ends (i.e., 150 and 152 of FIG. 1A) of the cryotherapy system are depicted without a center section. The securing mechanism 108 discussed with reference to FIGS. 1A-1D may alternatively include one or more metal hooks 802 (108A) as depicted in FIG. 8A, a set of snaps 806/808 (108B) as depicted in FIG. 8B, or a belt tightening system 810/812 (108C) as depicted in FIG. 8C (These securing mechanisms 108A, 108B, and 108C along with the securing mechanism 108 of FIGS. 1A-1D are generally referred to as securing mechanisms 108).

In some alternative embodiments, securing mechanism 108 may include a set of buttons, a binding or tethering system, or another suitable mechanism that may perform the functions described herein.

In each of FIGS. 8A-8C and as best illustrated in FIG. 1D, the securing mechanisms 108 include components that allow some adjustability when securing the cryotherapy system 100 to the user 104. For example, in FIG. 8A, the metal hooks 802 may be secured within multiple hook receivers 804. The hook receivers 804 are positioned in three separate rows, which allow three separate dimensions for the opening 106. Consequently, the cryotherapy system 100 may be positioned on the user 104 on an injured area and may be adjusted for the comfort of the user 104.

Similar to the metal hooks 108A, the set of snaps 108B in FIG. 8B includes snaps 806 and multiple snap receivers 808. The multiple snap receivers 808 are positioned in multiple rows, which allows adjustability in securing the cryotherapy system 100 to the user 104. Likewise, the belt tightening system 108C depicted in FIG. 8C includes belts 810 that are run through multiple buckles 812, which allows the belts 810 to be tightened. Additionally, the securing mechanism 108 of FIGS. 1A-1D includes multiple strips of hooks and multiple strips of loops that allow adjustment in the dimensions of the opening 106 and thus an adjustable fit of the cryotherapy system 100 on the user 104. By including some adjustability, an external pressure may be applied with little constriction of the cryotherapy system 100.

Figures 6A, 6B:
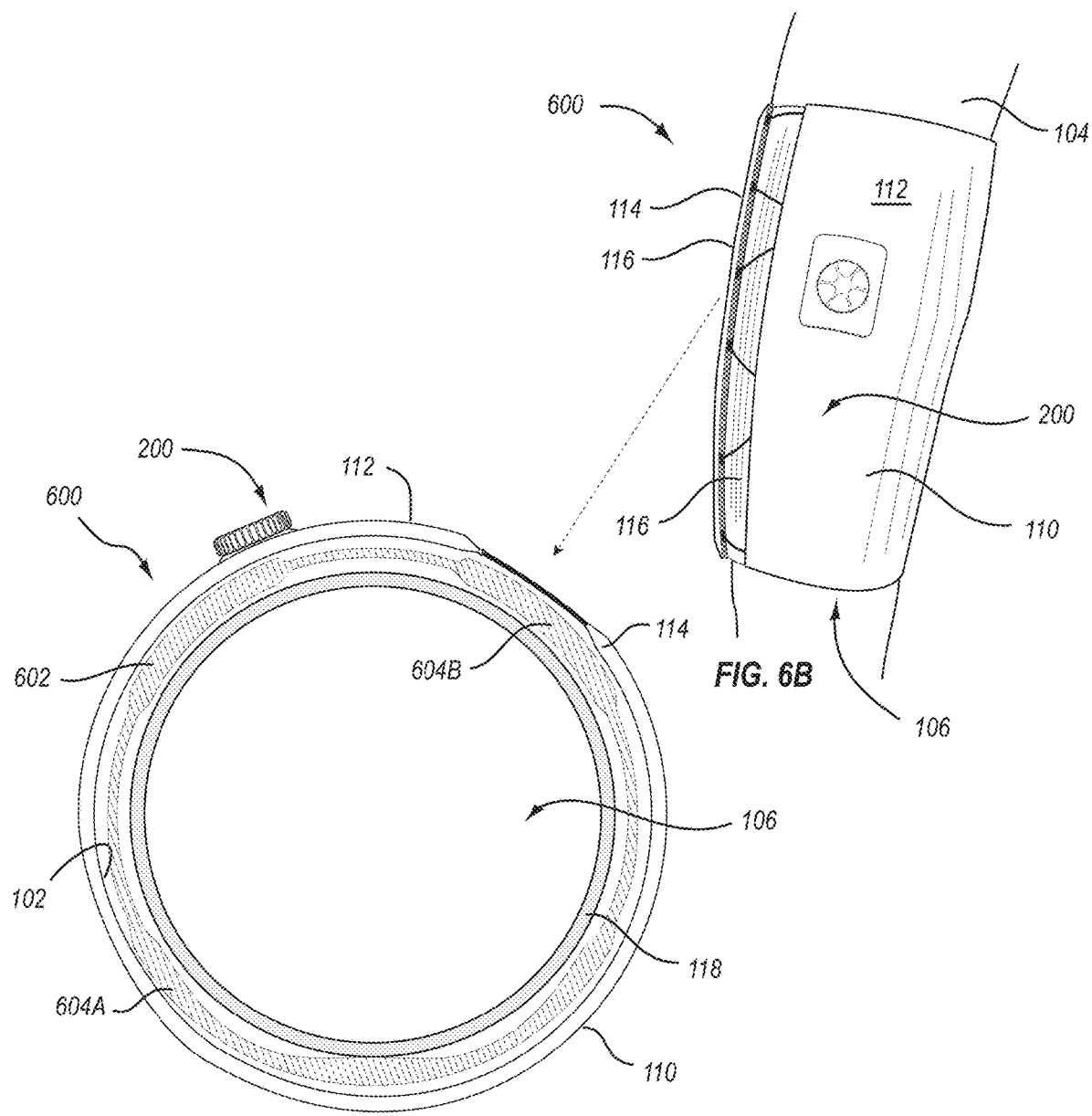
FIGS. 6A and 6B illustrate an example sleeve cryotherapy system implementing an example foam pad.

Alternatively, in some embodiments, the cryotherapy system 100 does not include a securing mechanism 108. For example, FIGS. 6A and 6B illustrate an embodiment of the cryotherapy system 100 that does not include a securing mechanism 108, which is referred to herein as a sleeve cryotherapy system 600. In these and other embodiments, the sleeve cryotherapy system 600 may be sized to fit a particular subset of users, e.g., small, medium, and large. Some additional details of a sleeve cryotherapy system 600 of FIGS. 6A and 6B are included below.

Referring back to FIGS. 1A-1D, the cryotherapy system 100 also includes an outer layer 110. The outer layer 110 further includes a first portion 112 and a second portion 114 which are interrupted by a separation 116. The outer layer 110 is attached to the inner layer 102 at the first portion 112 and the second portion 114 but not at the separation 116. For example, the first portion 112 and the second portion 114 of the outer layer 110 may be sewn to, adhered to, or otherwise attached to the inner layer 102. Thus, the separation 116 may be spanned by a piece of fabric and/or other material (the "spanning material") and the spanning material, in some embodiments at least, comprises an element of the compression layer. In yet other embodiments, the spanning material is not part of the compression layer and, instead is part of a layer situated inside of the compression layer.

Additionally, as best illustrated in FIGS. 1A-1C the securing mechanism 108 may be at least partially attached to the outer layer 110. For example, referring to FIG. 1B, when the cryotherapy system 100 is secured to the user 104 the first portion 112 may include one of the hooks or the loops and the second portion 114 may include the other of the hooks and the loops. The user 104 can thus wrap the cryotherapy system 100 around an extremity such that the first portion 112 overlaps the second portion 114 where the securing mechanism 108 is located.

The cryotherapy system 100 also includes a cold pack 118 (FIGS. 1B and 1D only). The cold pack 118 may be positioned between the inner layer 102 and the outer layer 110. The cold pack 118 may include, but is not limited to, a reusable self-contained chemical cold compress, a thermodynamic gel, a bag that may be filled with water, a bag that can be filled with ice, or a cold therapy water circulation system.

As illustrated in FIG. 1D, the cold pack 118 may be removable. In these embodiments, the inner layer 102 may include a zipper or hook and loop system to secure the cold pack 118 within the inner layer 102. Additionally, in these and other embodiments, the cold pack 118 may be removed and frozen then placed in the inner layer 102 before the cryotherapy system 100 is secured to the user 104. Alternatively, the cold pack 118 may be sewn into the inner layer 102. In these and other embodiments, the entire cryotherapy system 100 may be frozen prior to securing the cryotherapy system 100 to the user 104. Moreover, and as noted elsewhere herein, the cold pack 118 need not be employed in every case, and the cryotherapy system 100 can be used to provide compression only.

The cryotherapy system 100 also includes a tightening mechanism 200. In general, and as disclosed in more detail elsewhere herein, embodiments of a tightening mechanism, including the example tightening mechanism 200, are configured and operable to effect translational motion of one part of a device, such as cryotherapy system 100 for example, relative to another part of the device. The static portion of such an arrangement may comprise a first layer or sleeve, and the moving portion of such an arrangement may comprise a second layer, which can be a compression layer for example. The moving portion of the layer may also translate relative to a therapeutic device and/or one or more other layers of the device. In another example, only a single layer is used, and a tightening mechanism is configured and operable to effect translational movement of one portion of that layer relative to another portion of that layer. It should be noted that, as used herein, the compression layer refers to the layer whose portion, or portions, are moved by a tightening mechanism.

As well, this disclosure contemplates that any device, such as the cryotherapy system 100 for example, within the scope of this disclosure may include multiple tightening mechanisms, such as the example tightening mechanism 200. Such an arrangement may be useful where, for example, there is a need to exert different levels of compression on different portions of the anatomy of a user. By employing multiple, independently controllable, tightening mechanisms, even where a single tightening mechanism might otherwise suffice, such devices enable the implementation of highly customizable, and adjustable, compression schemes. As well, desirable useful therapeutic effects may be achieved in some instances by tightening the multiple tightening mechanisms in a particular order. For example, if multiple tightening mechanisms are to be used to compress a portion of the leg of a user, it may be desirable to tighten a tightening mechanism near the ankle of the user prior to tightening a tightening mechanism near the upper calf of the user. The multiple tightening mechanisms used in devices that include them may be the same as each other, or may be different from each other.

With the foregoing points in mind, details are now provided concerning some example tightening mechanisms, one of which is the tightening mechanism 200. In this particular example, the tightening mechanism 200 is configured and operable to move the first portion 112 of the outer layer 110 towards the second portion 114 of the outer layer 110, such that the first portion 112 slides along the outside of the cold pack 118. By moving the first portion 112 towards the second portion 114 the cold pack 118 is pressed against inner layer 102, and an external pressure is applied to the user 104. The external pressure may be a therapeutic compression and the external pressure may press the cold pack 118 against the extremity of the user 104 to increase thermodynamic transfer from the extremity of the user 104.

Additionally, the tightening mechanism 200 is configured to maintain the position of the first portion 112 with respect to the second portion 114. Thus, when the user 104 applies the external pressure, the tightening mechanism 200 holds a constant or semi-constant external pressure on the injured area. By maintaining the first portion 112 with respect to the second portion 114, the therapeutic benefits of the external pressure and the thermodynamic transfer is applied for a controllable duration without additional efforts by the user 104.

Referring to FIG. 1C, an overview of an example function of the cryotherapy system 100 is illustrated. The cryotherapy system 100 may be applied to the user 104 in a first arrangement. In the first arrangement, the tightening mechanism 200 is loose (i.e., the separation 116 is at its greatest dimension), allowing the user 104 to introduce an extremity in to the opening 106. In the first arrangement, the user 104 may generally position the cryotherapy system 100 over an injured area.

The user 104 then tightens the tightening mechanism 200, which moves the first portion 112 of the outer layer 110 towards the second portion 114 of the outer layer 110. The tightening mechanism 200 places the outer layer 110 in tension, reduces the dimension of the separation 116, and reduces the dimension of the opening 106. Due to the reduction in the dimension of the opening 106, an external pressure is imposed on the extremity introduced into the opening 106.

Figure 2:
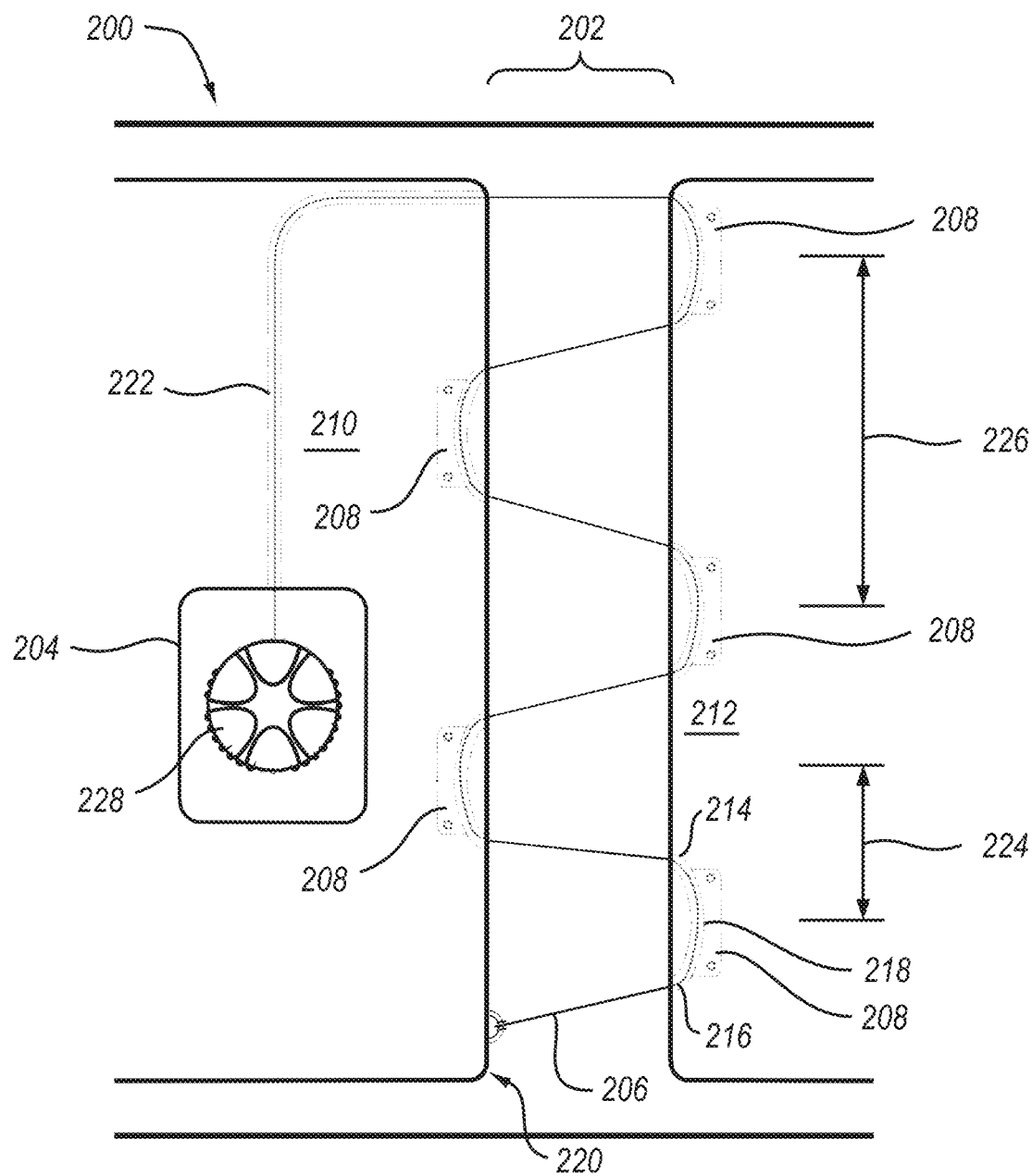
FIG. 2 illustrates an example tightening mechanism that may be implemented in the cryotherapy system of FIGS. 1A-1D.

FIG. 2 illustrates an example tightening mechanism 200 that may be implemented in the cryotherapy system 100 of FIGS. 1A-1D. The tightening mechanism 200 may be implemented, for example, on the outer layer 110 of the cryotherapy system 100 of FIGS. 1A-1D. Some examples of such a tightening mechanism include tightening mechanisms by Boa Technology, Inc. (http://www.boatechnology.com/), although other tightening mechanisms can alternatively be employed.

It will be appreciated from the present disclosure that the example tightening mechanisms disclosed herein are example structural embodiments of a means for applying and controlling pressure, and any other structural element(s) capable of performing one or more aspects of the functionality of the disclosed tightening mechanisms may alternatively be employed and are considered to be within the scope of this disclosure.

Generally, the tightening mechanism 200 includes a lace 206 that is routed through one or more lace retainers 208. Some of the lace retainers 208 are positioned on a first portion 210 and the other lace retainers are positioned on a second portion 212. The lace 206 is retracted by a lace tensioner 204. As the lace 206 is refracted, tension is applied to the lace retainers 208, moving the first portion 210 towards the second portion 212.

In FIG. 2, the lace tensioner 204 includes a rotate-and-lock mechanism 228. The rotate-and-lock mechanism 228 may enable a user to rotate an external piece that winds the lace 206. As the lace 206 is wound, the rotate-and-lock mechanism 228 maintains the lace 206 until released by the user. In some embodiments, the rotate-and-lock mechanism 228 may be geared such that one rotation of the external piece results in multiple rotations of a spool on which the lace 206 is wound.

Embodiments of the tightening mechanism 200 are not limited to a rotate-and-lock mechanism 228. FIGS. 3A-3C illustrate example lace tensioners 300A, 300B, and 300C (generally lace tensioner 300 or lace tensioners 300) that may be implemented in the tightening mechanism of FIG. 2. Each of the lace tensioners 300 may be included in a tightening mechanism, which is similar to the general configuration described above with respect to FIG. 2. To apply tension to the lace 206, each of the lace tensioners 300 retract the lace 206 and maintain the position of the lace 206 as refracted until released by a user.

Specifically, FIG. 3A depicts a pull-and-lock mechanism 300A that may be implemented as a lace tensioner. To apply tension to the lace 206, the user pulls as indicated by arrow 302. As the lace 206 moves through a locking mechanism, pressure is applied to the lace 206 to maintain the position of the lace 206 until a user releases the locking mechanism 304.

FIG. 3B depicts a wind-and-tuck mechanism 300B that may be implemented as a lace tensioner. To apply tension to the lace 206, the user winds a handle 306, which retracts the lace 206. The user then tucks the handle 306 into a receiver 308 that prevents the handle 306 from un-winding. The tension is maintained until a user removes the handle 306 from the receiver 308.

FIG. 3C depicts a jam cleat 300C that may be implemented as a lace tensioner. To apply tension to the lace 206, the user pulls on a handle 310 connected to the lace 206. A cleat 312 allows the lace 206 to move through the cleat 312 in one direction but prevents movement in the opposite direction. Thus, the tension is maintained until a user releases the cleat 312.

Referring back to FIG. 2, the lace 206 may be composed of various materials and/or may include a coating composed of various materials. Selection of material for the lace 206 and/or the material for the coating may be based on the lace tensioner 204. Some lace tensioners 204 may be geared to increase the tension in the lace 206. In these and other embodiments, the material for the lace 206 and/or the coating may be selected to withstand the tension.

Additionally or alternatively, the material of the lace 206 and/or the coating may be selected to affect friction between the lace 206 and the lace retainers 208. As the lace 206 is drawn through the lace retainers 208, there may be some advantages of having friction between the lace retainer 208 and the lace 206. For instance, friction between the lace 206 and the lace retainer 208 may result in sequential tightening which is described with reference to FIGS. 4A and 4B, while reducing friction between the lace 206 and the lace retainer 208 may result in a more even tension between the lace retainers 208.

In the depicted embodiment, the lace retainers 208 are U shaped. Specifically, each of the lace retainers 208 includes an inlet 214, an outlet 216, and a length 218. The inlet 214 and the outlet 216 are oriented substantially perpendicular to edges 220 of the first portion 210. The length 218 is oriented substantially parallel to the edges 220 of the first portion 210. In FIG. 2, the inlet 214, the outlet 216 and the length 218 are labeled on one lace retainer 208, however each of the lace retainers 208 include an inlet, an outlet 216 and a length 218.

In some embodiments, the lace retainers 208 positioned on the first portion 210 are staggered with respect to the lace retainers 208 positioned on the second portion 212. In these and other embodiments, inlets 216 of the lace retainers 208 on the first portion 210 may be positioned across the separation 202 from outlet 212 of the lace retainers 208 on the second portion 212. Alternatively, the lace retainers 208 positioned on the first portion 210 may be positioned directly opposite a corresponding lace retainer 208 positioned on the second portion 212.

A first distance 224 may be defined between any one of the lace retainers 208 on the first portion 210 and any one of the lace retainers 208 on the second portion 212. Additionally, a second distance 226 may be defined between any one of the lace retainers 208 on the first portion 210 and any other, adjacent lace retainers 208 on the first portion or between any one of the lace retainers 208 on the second portion 212 and any other, adjacent lace retainers 208 on the second portion 212. The first distance 224 and the second distance 226 may vary between embodiments and may vary on a single embodiment. For example, a first distance 226 and a second distance 224 may include one inch near the edge 220 and two inches farther from the edge 220. This may create differing pressures in different areas when the tightening mechanism 200 is operated. When the lace retainers 208 are closer together (i.e., the first and/or second distances 226 and 224 are smaller) more pressure may result and when the lace retainers 208 are farther from one another, less pressure may result. Additionally, the number of lace retainers 208 may vary between embodiments. The number of lace retainers 208, the first distance 224 and the second distance 226 may be selected to create areas of high tension and areas of low tension, to create different areas of mobility, etc.

The tightening mechanism 200 may also include a lace conduit 222. The lace conduit 222 is coupled to the lace tensioner 204 at one end and routes the lace 206 to the edge 220 of the first portion 210. The lace conduit 222 may be configured to such that the lace tensioner 204 may be positioned in a convenient location on the first portion 210. Additionally, the lace conduit 222 can be configured such that the lace 206 exits the lace conduit 222, extends across the separation 202, and enters one of the lace retainers 208.

In some embodiments, the lace conduit 222 may be configured such that the lace 206 extends across the separation 202 at a substantially right angle to the edge 220 of the first portion 210.

FIGS. 4A-4C illustrate an example sequential tightening process that may be implemented by the tightening mechanism 200 of FIG. 2. Accordingly, some of the components described with respect to FIG. 2 are included in FIGS. 4A-4C. Description of these components is not repeated with reference to FIGS. 4A-4C.

FIGS. 4A-4C illustrate a sequence of views 400A-400C of the tightening mechanism 200 of FIG. 2 as tension is applied to a lace 206. FIG. 4A illustrates a first view 400A in which the tightening mechanism 200 has little or no tension applied to the lace 206. FIG. 4B illustrates a second view 400B in which the tightening mechanism 200 has some tension applied to the lace 206. FIG. 4C illustrates a third view 400C in which the tightening mechanism 200 has a tension applied and maintained.

FIGS. 4A-4C include a user 402 and a cryotherapy system is fit to a leg of the user 402. The leg of the user 402 is oriented in FIGS. 4A-4C such that a core of the user 402 is above (i.e., at the top of each of FIGS. 4A-4C) the cryotherapy system. The lace retainers 208 include one or more proximate lace retainers 404 positioned nearest the core of the user 402 and one or more distal lace retainers 406 positioned farthest from the core of the user 402.

As shown in FIG. 4B, when the tightening mechanism applies tension to the lace 206, the distal laces 406 retainers move together before the proximate lace retainers 404. Accordingly, an exterior pressure is applied first to the user 402 away from the core of the user 402. The tension is sequentially applied, distal-most lace retainers 406 to proximate-most lace retainers 404. As depicted in FIG. 4C, once the tension is applied and maintained, the external pressure becomes uniform.

By applying tension in a distal-to-proximal fashion, namely, from a portion of the anatomy of the user most remote from the core of the user to a portion of the anatomy of the user relatively nearer to the core of the user, embodiments of the tightening mechanism can facilitate healing and/or recovery processes.

Figure 5A:
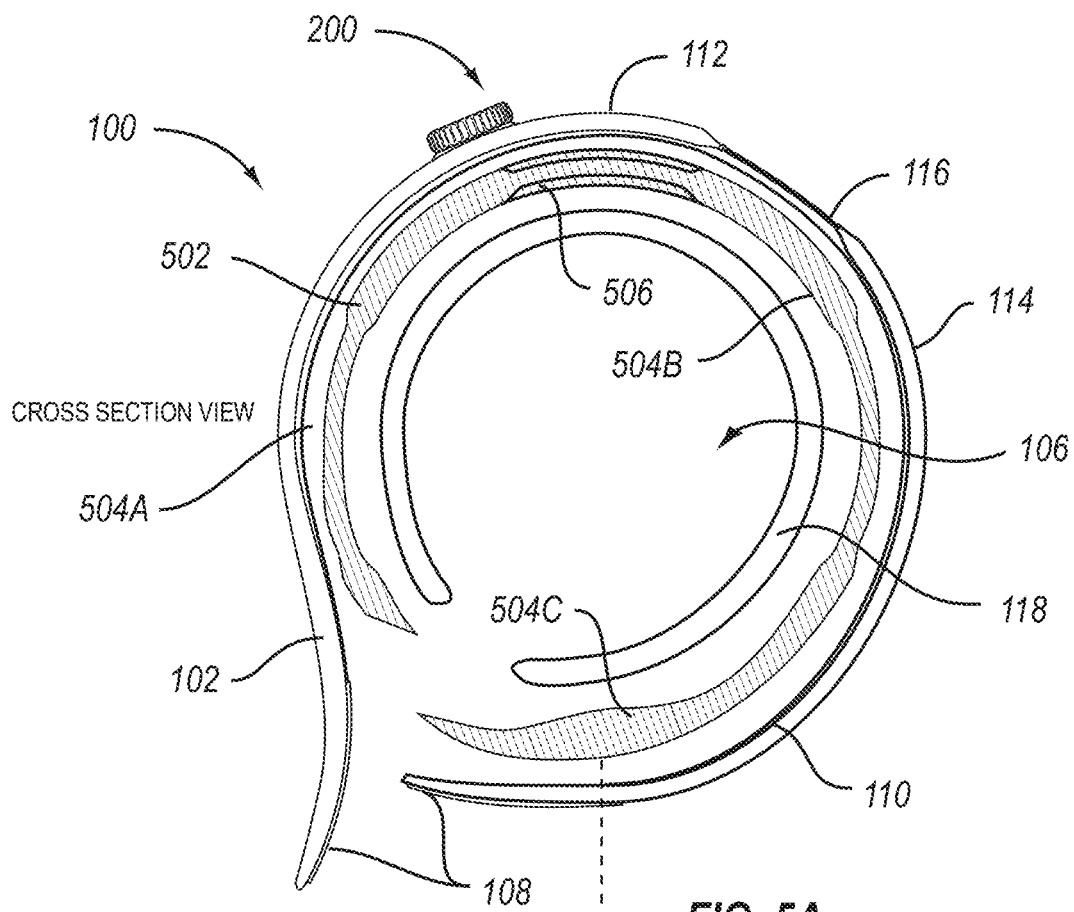
FIGS. 5A and 5B illustrate an example foam pad that may be implemented in the cryotherapy system of FIGS. 1A-1D.
Figure 5B:
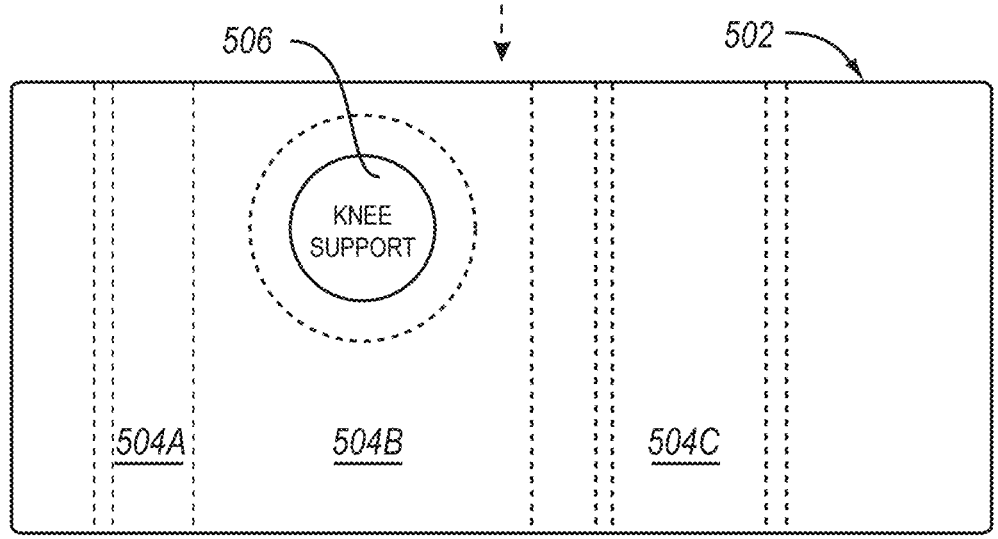

FIGS. 5A and 5B illustrate implementation of an example foam pad 502 in the cryotherapy system 100 of FIGS. 1A-1D. FIG. 5A include components (e.g., 102, 200, 112, 116, 114, 106, 118, 110, and 108) described with reference to FIGS. 1A-1D. Descriptions of these components are not repeated with reference to FIG. 5A.

It should be noted that embodiments of a foam pad, such as foam pad 502 and 602 for example, can be supplemented with, or replaced by, a plurality of smaller pads of the same, or different, material as the foam pad 502 and foam pad 506. In some instances, an embodiment of the invention can be provided with a packet of smaller pads of various shapes and sizes that a user can use to customize the device to his or her particular anatomy. For example, a knee joint includes a variety of different shapes and surfaces, and one or more different pads, such as a pad having a butterfly shape for example, can be placed at the appropriate locations of the device to ensure that all of the shapes and surfaces of the knee joint are compressed at substantially the same time, and with substantially the same magnitude of compressive force, as other parts of the anatomy with which the device is in contact.

These pads can be of a material that is relatively easy to cut, such as with scissors. Additionally, the pads can be configured to be removably attached to a portion of the device, such as by a hook-and-loop type of material, so that they can easily be relocated to suit another user. In one alternative embodiment, the pads are permanently affixed to a layer of the device, such as by sewing. In this alternative, the pads can be located within the layer or on the outside of the layer. The layer that carries the pads can be the compression layer, or can be another layer located between the compression layer and the anatomy of the user.

Generally, the foam pad 502 acts to concentrate the external pressure to areas, which due to the natural shape of extremities, may otherwise not receive sufficient compression or thermodynamic transfer. With combined reference to FIGS. 5A and 5B, the foam pad 502 may include multiple thicknesses 504A-504C (generally thicknesses 504) and/or a hole 506. The thicknesses 504 and/or the hole 506 are positioned on the foam pad 502 to conform to or to correspond to a shape an extremity introduced into the opening 106. Thus, the positions of the thicknesses 504 and/or the hole 506 may be different depending on the particular embodiment.

In the cryotherapy system 100 of FIG. 5A, the inner layer 102 is formed on an inner surface of the outer layer 110. The foam pad 502 is positioned between the inner layer 102 and the cold pack 118. In alternative embodiments, the inner layer 102 may be configured to receive the cold pack 118 and the foam pad 502. In either configuration, the foam pad 502 is positioned between the outer layer 110 and the cold pack 118 such that external pressure is transferred from the outer layer 110 to the foam pad 502, to the cold pack 118, and against a user.

When the outer layer 110 applies external pressure (i.e., the first portion 112 of the outer layer 110 is moved towards the second portion 114 of the outer layer 110) through operation of the tightening mechanism 200, a first pressure is applied at a first area under a first thickness 504A, a second pressure is applied at a second area under the second thickness 504B, etc. The first thickness 504A, the second thickness 504B, the third thickness 504C, the hole 506, or some combination thereof may be applied to a low point of a joint on the extremity introduced to the opening 106.

FIGS. 6A and 6B illustrate an example sleeve cryotherapy system 600 implementing an example foam pad 602. The sleeve cryotherapy system 600 depicted in FIGS. 6A and 6B is substantially similar to the cryotherapy system 100 depicted in FIG. 5A. However, the sleeve cryotherapy system 600 omits the securing mechanism 108. Instead, the sleeve cryotherapy system 600 is slid onto the user 104 as depicted in FIG. 6B. Once slid onto the user 104, external pressure may be applied through operation of the tightening mechanism 200.

As in the embodiment described with respect to FIGS. 5A and 5B, the sleeve cryotherapy system 600 may include a foam pad 602 positioned between the outer layer 110 and the cold pack 118. When the external pressure is applied, the foam pad 602, which includes at least two thicknesses 604A and 604B, may concentrate the external pressure to one or more areas which may correspond to a low point or a high point of on the extremity introduced into the opening 106.

Figure 7A:
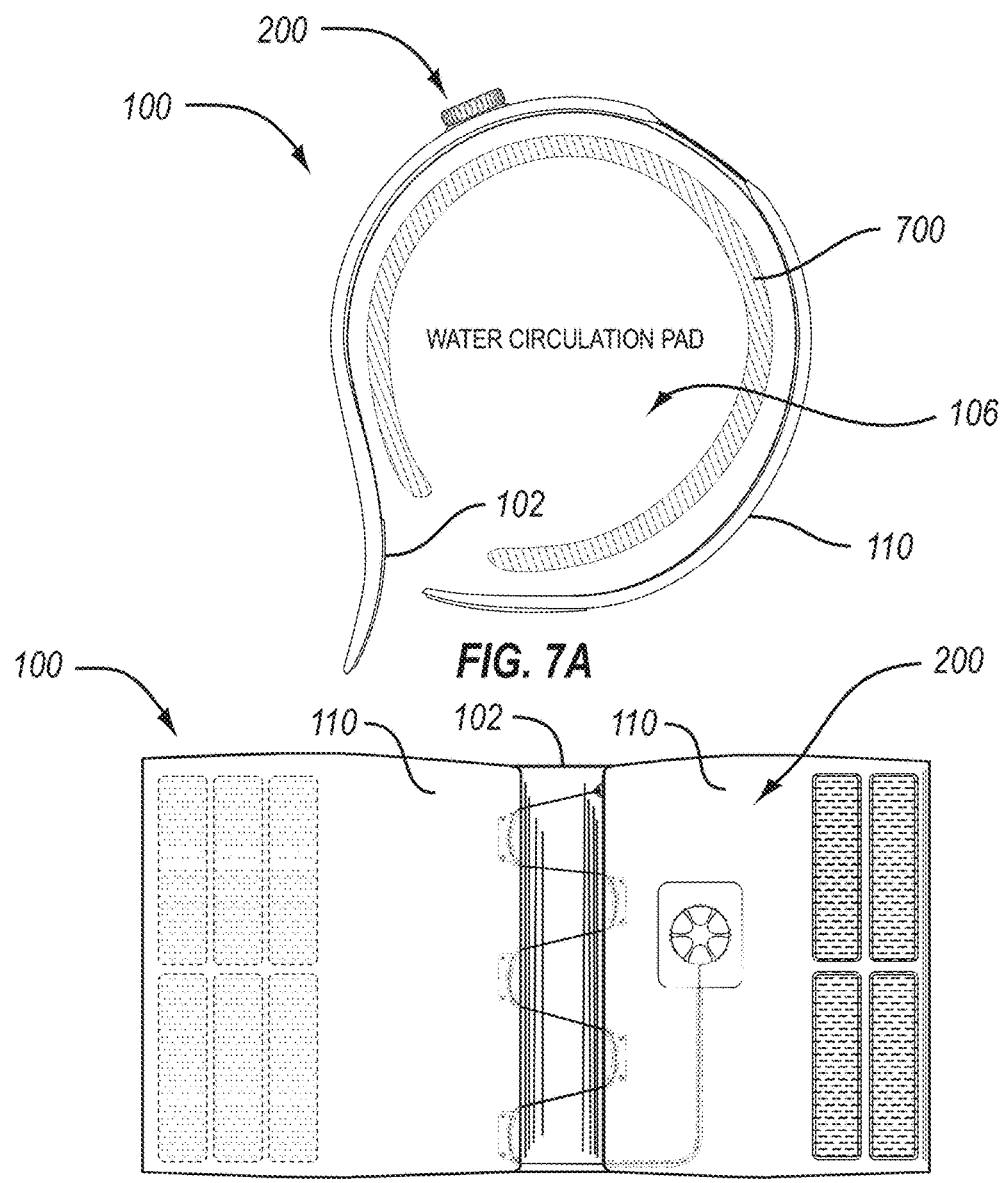
FIGS. 7A and 7B illustrate an example cold therapy water circulation system implemented in the cryotherapy system of FIGS. 1A-1D.
Figure 7B:
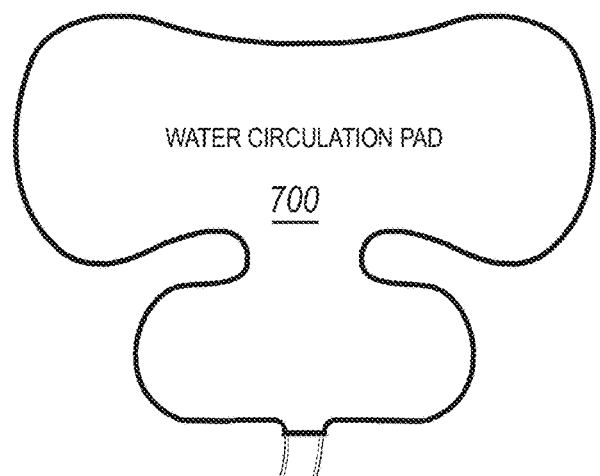

FIGS. 7A-7B illustrate implementation of an example cold therapy water circulation system 700 in the cryotherapy system 100 of FIGS. 1A-1D. FIGS. 7A and 7B include components (e.g., 102, 200, 110, and 106) described with reference to FIGS. 1A-1D. Descriptions of these components are not repeated with reference to FIGS. 7A and 7B.

In this and other embodiments, the cold therapy water circulation system 700 is substituted for the cold pack 118 of FIGS. 1A-1D. The cold therapy water circulation system 700 may be coupled to a circulation pump that supplies cooling water or a cooling gel to the cold therapy water circulation system 700. The cold therapy water circulation system 700 may be commercially available by a third party, in some embodiments.

The cold therapy water circulation system 700 may be positioned between the inner layer 102 and the opening 106 as shown in FIG. 7A. Alternatively, the cold therapy water circulation system 700 may be sewn into or may be removably secured within the inner layer 102.

Figures 9A, 9B:
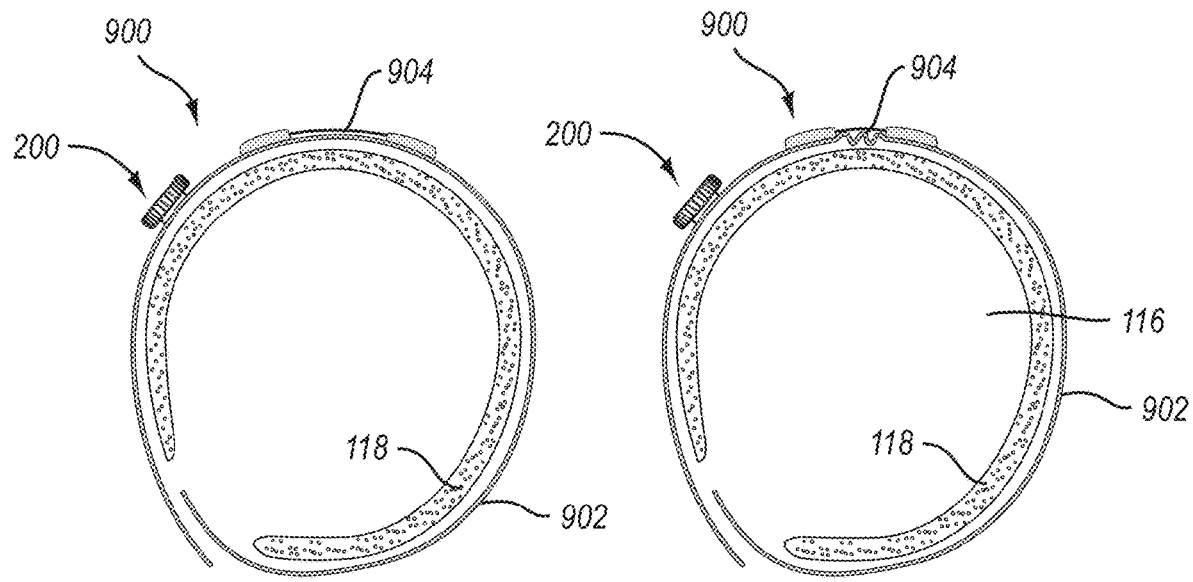
FIGS. 9A-9C illustrate an example continuous cryotherapy system.
Figure 9C:
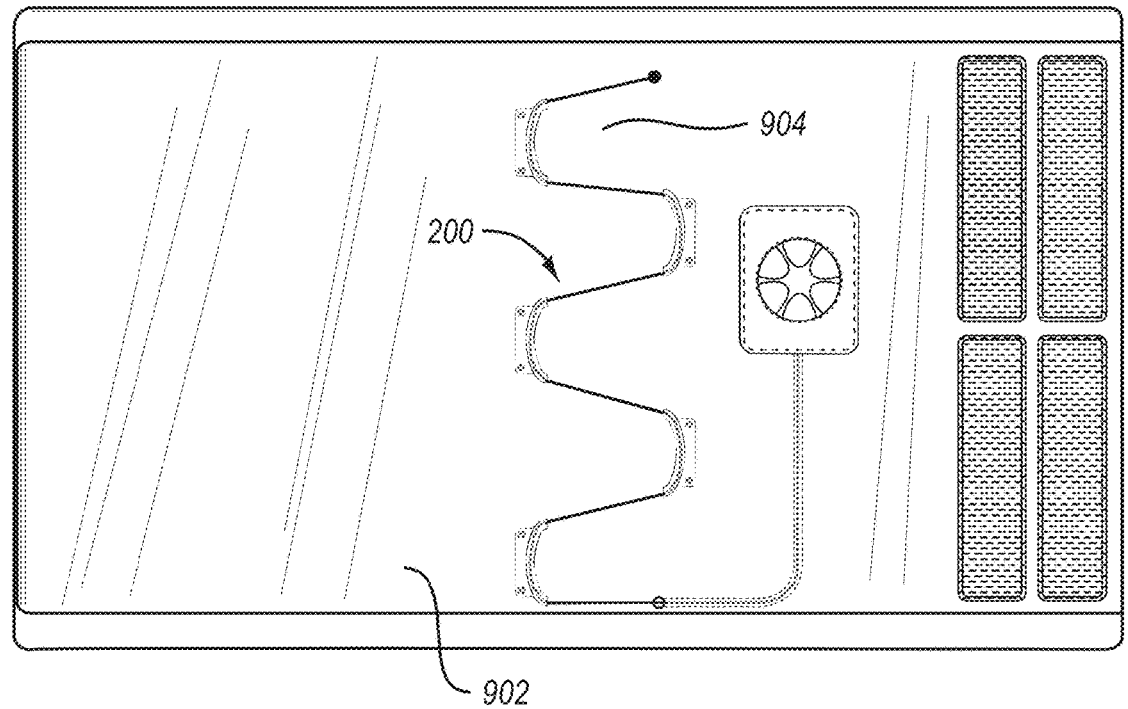

FIGS. 9A-9C illustrate an example continuous cryotherapy system 900. The continuous cryotherapy system 900 is similar to the cryotherapy system 100 described with reference to FIGS. 1A-1D. Accordingly, some components described with reference to FIGS. 1A-1D are included in FIGS. 9A-9C. FIG. 9A is a sectional view of the continuous cryotherapy system 900 with little or no tension in the tightening mechanism 200. FIG. 9B is a sectional view of the continuous cryotherapy system 900 with tension in the tightening mechanism 200. FIG. 9C is a view of the continuous cryotherapy system 900 un-wrapped.

The continuous cryotherapy system 900 includes a continuous layer 902 with no separation. The tightening mechanism 200 is attached to the continuous layer 902 across a narrowing portion 904 which is configured to gather when the tightening mechanism 200 imposes an external force on the continuous cryotherapy system 900. The narrowing portion 904 is shown gathered in FIG. 9B. When the tightening mechanism 200 imposes an external force by gathering the narrowing portion 904, the opening 116 is reduced and the cold pack 118 is pressed against an extremity introduced into the opening 116.

Figures 10A, 10B:
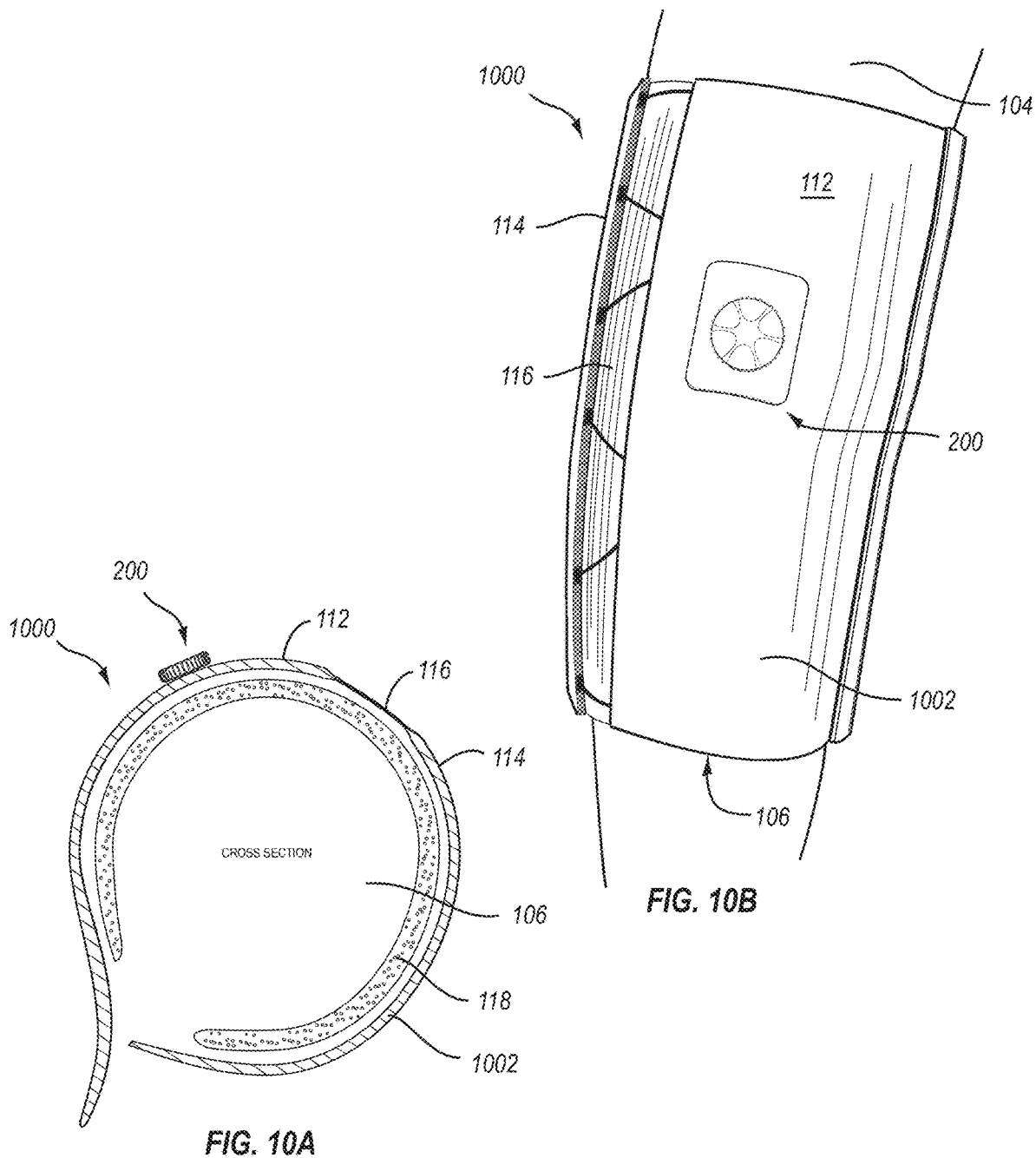
FIGS. 10A and 10B illustrate an example single-layer cryotherapy system.

FIGS. 10A and 10B illustrate an example single-layer cryotherapy system 1000. The single-layer cryotherapy system 1000 is similar to the cryotherapy system 100 described with reference to FIGS. 1A-1D. Accordingly, some components described with reference to FIGS. 1A-1D are included in FIGS. 10A and 10B. FIG. 10A is a sectional view of the single-layer cryotherapy system 1000. FIG. 10B is a view of the single-layer cryotherapy system 1000 applied to the user 104.

The single-layer cryotherapy system 1000 includes a single layer 1002 rather than the outer layer 110 and inner layer 102 described with reference to FIGS. 1A-1D. The single layer 1002 may include the first portion 112 and the second portion 114 with the separation 116 therebetween. The cold pack 118 may be positioned between the single layer 1102 and the user 104 such that when the tightening mechanism 200 applies and external force, the cold pack 118 is pressed against the user 104. In some embodiments, rather than having the single layer 1102 applying the external force to the cold pack 118, the cold pack 118 may be the single layer 1102. In these and other embodiments, the tightening mechanism 200 may be attached to the cold pack 118. For example, the tightening mechanism 200 may be adhered directly to an outer surface of the cold pack 118.

Alternatively, with combined reference to FIGS. 9A-10B, the single layer 1102 may be configured without the separation 116 (i.e., include a continuous layer similar to 902). Like in FIGS. 9A and 9B, the tightening mechanism 200 is attached to the singly layer 1002 across a narrowing portion 904 which gathers when the tightening mechanism 200 imposes an external force.

Figures 11A, 11B:
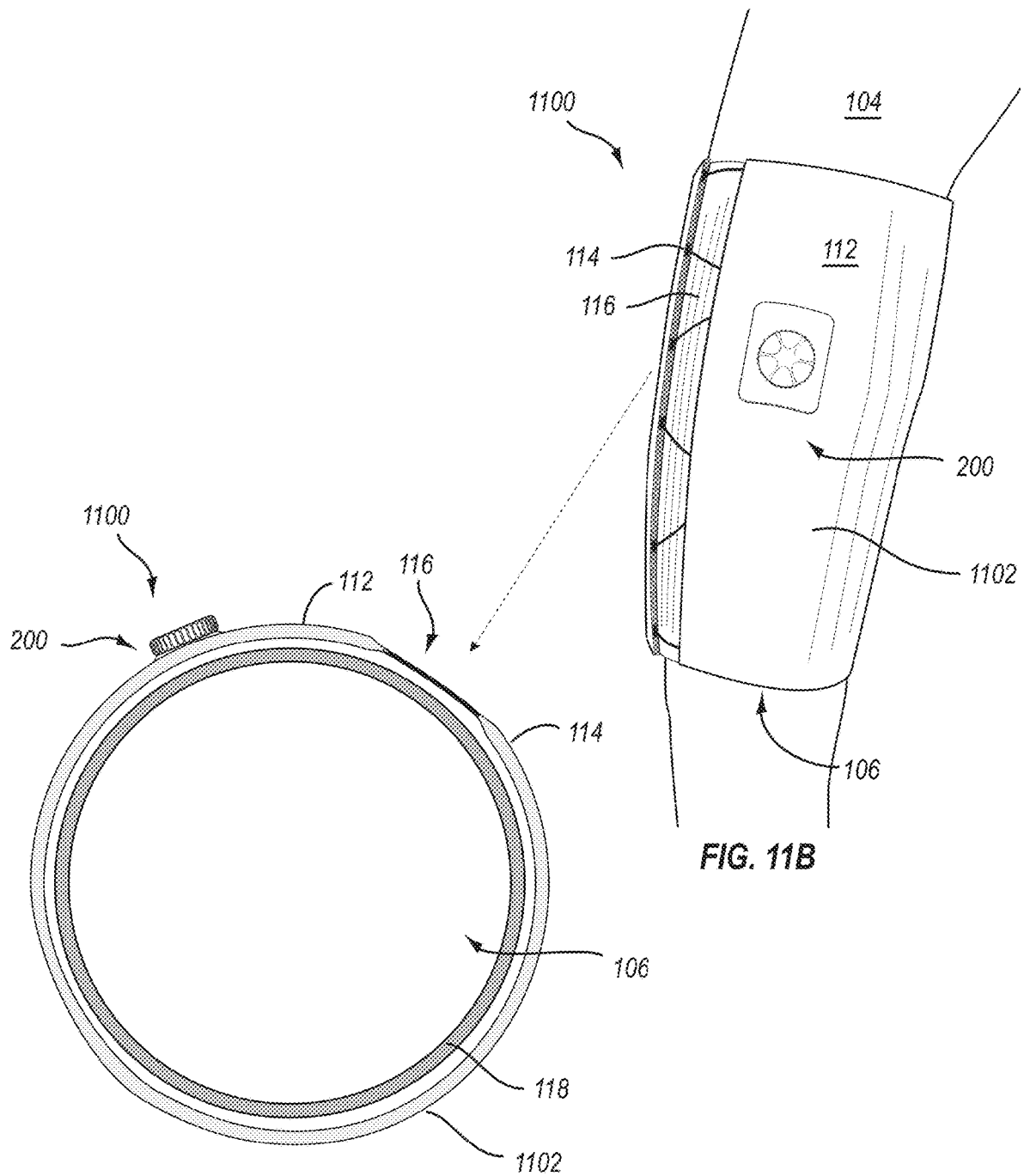
FIGS. 11A and 11B illustrate another example sleeve cryotherapy system.

FIGS. 11A and 11B illustrate another example sleeve cryotherapy system 1100. The sleeve cryotherapy system 1100 is similar to the sleeve cryotherapy system 600 described with reference to FIGS. 6A and 6B. Accordingly, some components describe with reference to FIGS. 6A and 6B are included in FIGS. 11A and 11B. FIG. 11A is a sectional view of the sleeve cryotherapy system 1100. FIG. 11B is a view of the sleeve cryotherapy system 1100 applied to the user 104.

The sleeve cryotherapy system 1100 includes a single outer sleeve 1102 which surrounds the cold pack 118. The sleeve cryotherapy system 1100 does not include a foam pad such as the foam pad 602 in the sleeve cryotherapy system 600 described with reference to FIGS. 6A and 6B. The single outer sleeve 1102 may include the separation 116, the first and second portions 112 and 114 or may be a continuous layer (not shown) similar to the continuous cryotherapy system 900 of FIGS. 9A and 9B.

Figure 12:
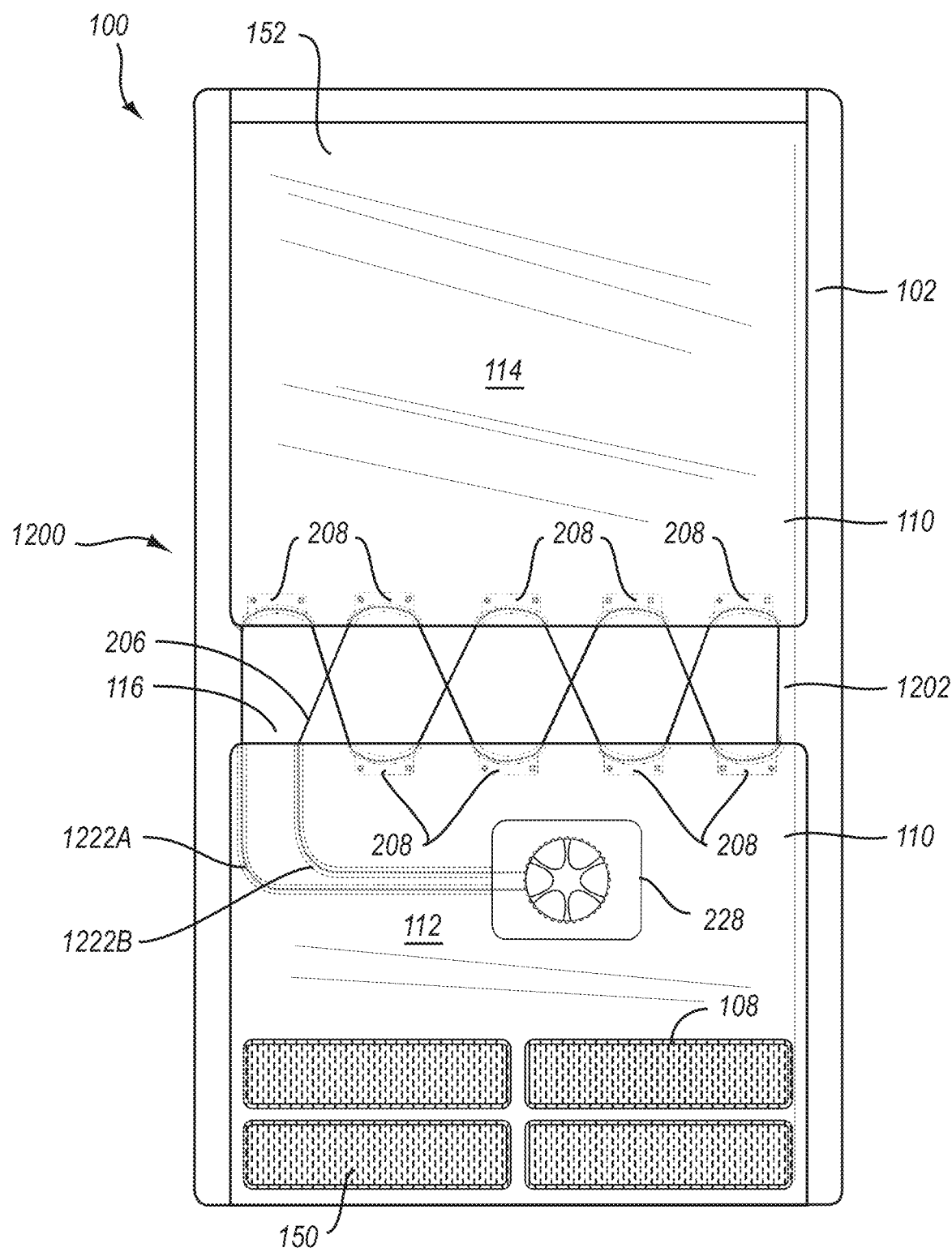
FIG. 12 illustrates another example tightening mechanism that may be implemented in the cryotherapy system of FIGS. 1A-1D.

FIG. 12 illustrates another example tightening mechanism 1200 that may be implemented in the cryotherapy system 100 of FIGS. 1A-1D or the systems 600, 900, 1000, 1100 described with reference to FIGS. 6A, 6B, and 9A-11B. The tightening mechanism 1200 is similar to the tightening mechanism 200 described with reference to FIG. 2. Accordingly, FIG. 12 includes components described with reference to FIG. 2. The tightening mechanism 1200 is shown in FIG. 12 implemented in the cryotherapy system 100 of FIG. 1A-1D.

The tightening mechanism 1200 includes a doubled-back lace configuration 1202. In the doubled-back lace configuration 1202, the lace 206 exits a first conduit 1222A and is routed through multiple lace retainers 208 (only the lace retainers 208 on the first portion of the outer layer 110 are labeled). The lace 206 is then routed back through the lace retainers, through a second conduit 1222B and to the rotate-and-lock mechanism 228. Like the embodiments described below, in the tightening mechanism 1200, the lace retainers 208 may be evenly spaced or one or more distances between the lace retainers 208 may vary. In embodiments, with variable distances, the positions of one or more lace retainers 208 may be determined to create areas with high or low pressures.

Figure 13B:
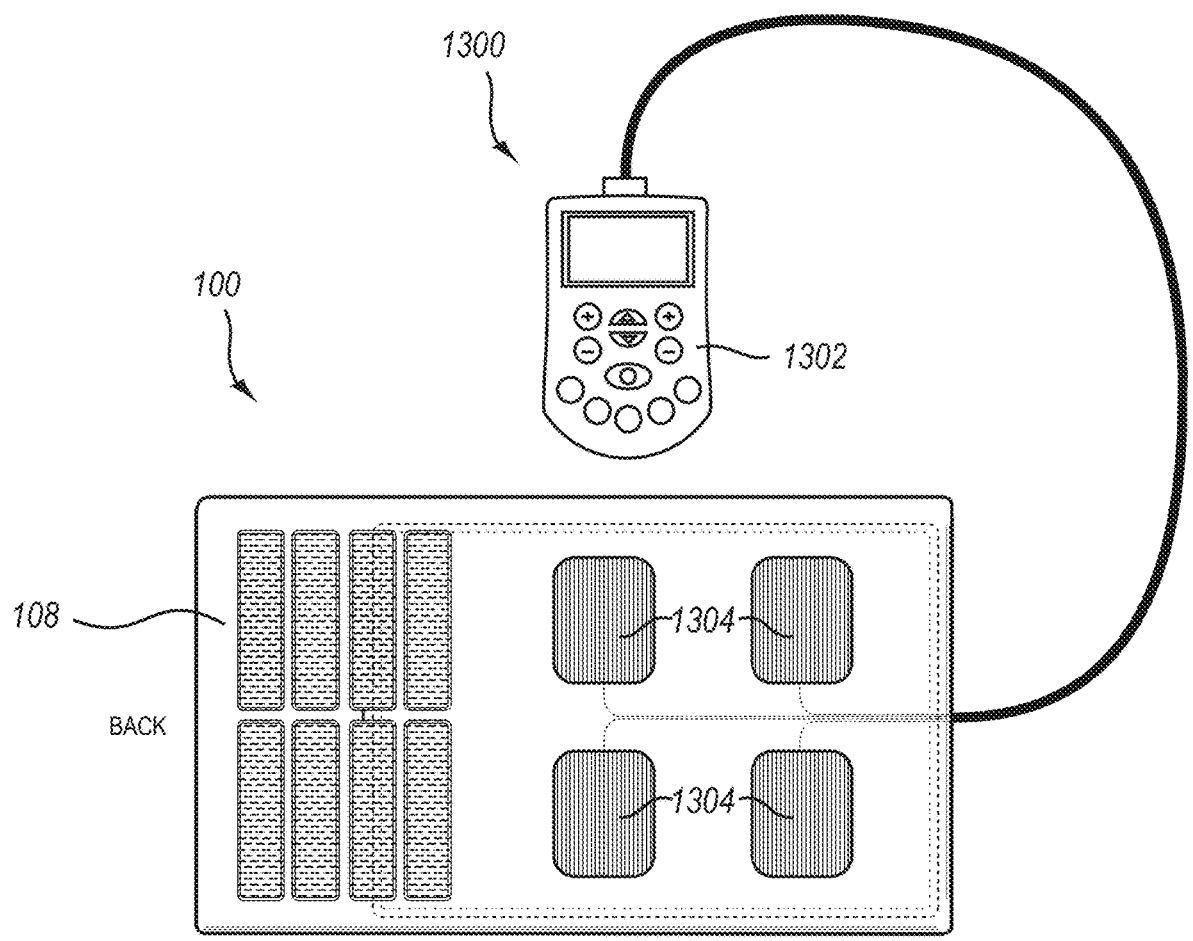
FIGS. 13A and 13B illustrates an example transcutaneous electrical nerve stimulation unit implemented in the cryotherapy system of FIGS. 1A-1D.
Figure 13A:
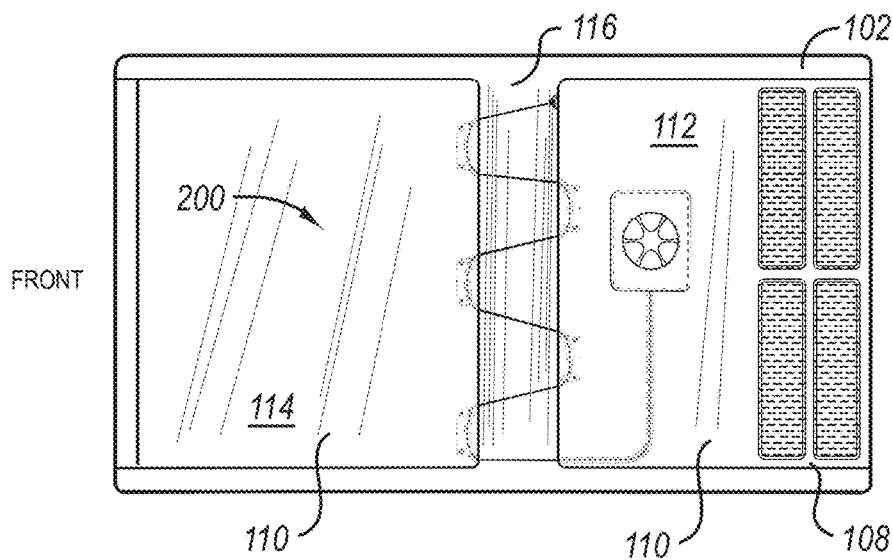

FIGS. 13A and 13B illustrate an example transcutaneous electrical nerve stimulation (TENS) unit 1300 implemented in the cryotherapy system 100 of FIGS. 1A-1D. Accordingly, some components described with reference to FIGS. 1A-1D are included in FIGS. 13A and 13B. FIG. 13A is a front view of the cryotherapy system 100 un-wrapped and FIG. 13B is a rear view of the cryotherapy system 100.

The TENS unit 1300 may include a controller 1302 and one or more contact pads 1304. The controller 1302 supplies electrical stimulation to muscle fibers in contact with the contact pads 1304. The TENS unit 1300 may be sewn into the inner layer 102, the outer layer 110 or some combination thereof such that contact pads 1304 contact skin of a user. Alternatively, the contact pads 1304 may be removable. For instance, the contact pads 1304 may include a hook and loop system that enables the contact pads 1304 to be positioned to supply the electrical stimulation to an injured area.

Alternatively, the TENS unit 1300 may be implemented in the sleeve cryotherapy system 1100, the continuous cryotherapy system 900, the single-layer cryotherapy system

1000, or any of the embodiments depicted in FIGS. 14-19B. Additionally, the TENS unit 1300 may be implemented in any of the above system (e.g., 100, 900, 1000, 1100, etc.) with or without the cold compress 118.

Figure 14:
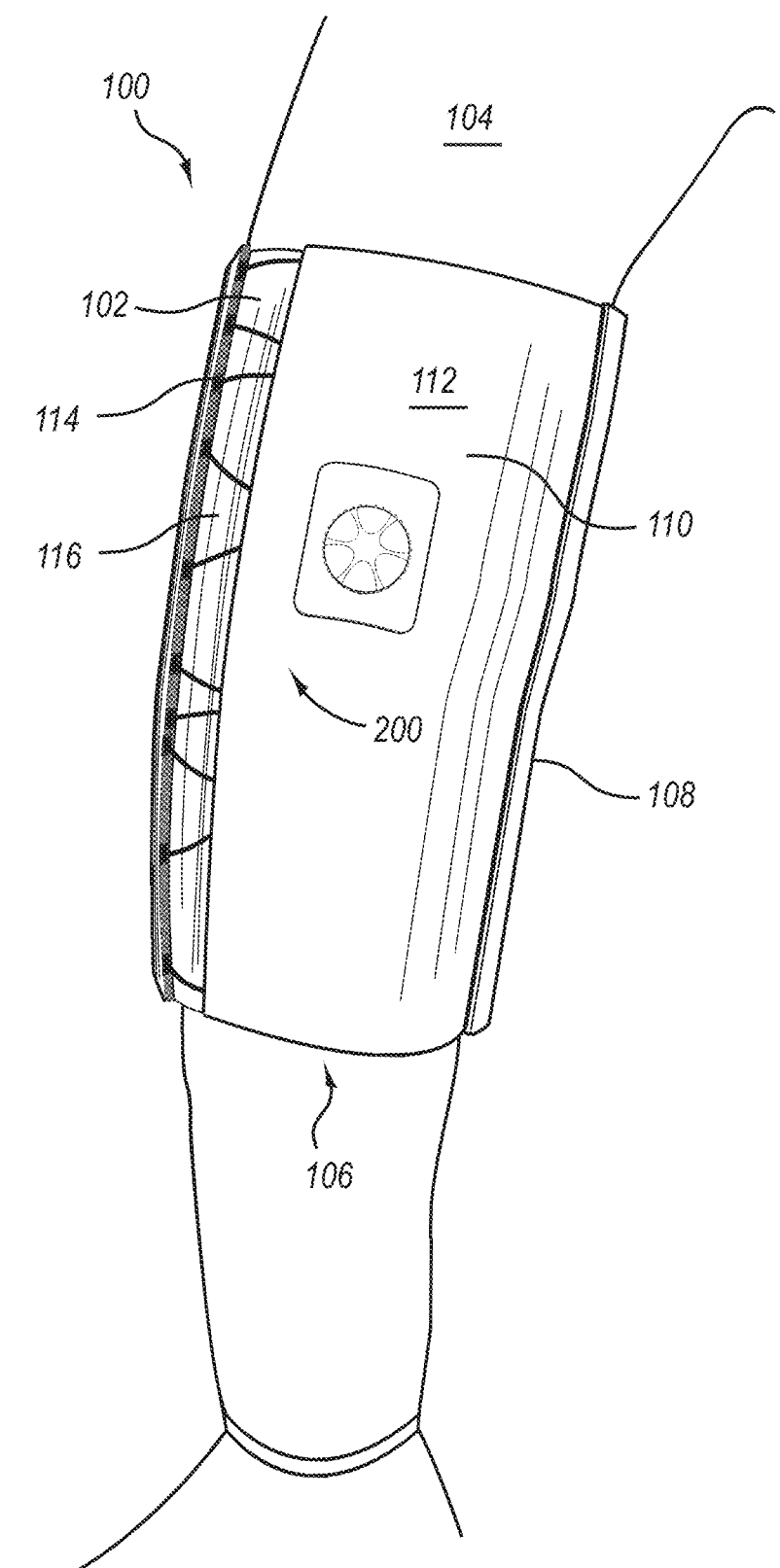
FIG. 14 illustrates an example cryotherapy system of FIGS. 1A-1D configured to fit a knee.

FIG. 14 illustrates an example cryotherapy system 100 of FIGS. 1A-1D configured to fit a knee of the user 104. Specifically, FIG. 14 is a perspective view of the cryotherapy system 100 configured to fit a knee. As illustrated in FIG. 14, when configured to fit a knee, the securing mechanism 108 may be positioned along a rear portion of the cryotherapy system 100 and the tightening mechanism 200 may be positioned along a front portion of the cryotherapy system 100. The cryotherapy system 100 wraps around the knee of the user 104. The tightening mechanism 200 may then apply external pressure to the knee of the user 104.

When the cryotherapy system 100 is configured to fit a knee, the cold pack (not shown), the inner layer 102, the outer layer 110, etc. may take shapes to conform to the shape of the knee. The cryotherapy system 100 configured to fit a knee may include foam pads as described in FIGS. 5A-6B, may omit the securing mechanism 108, may implement alternative securing mechanisms 108 described with reference to FIGS. 8A-8C, may include a cold therapy water circulation system as described with reference to FIGS. 7A and 7B, or any combination thereof. Additionally or alternatively, the tightening mechanism 200 may include jam cleat, wind-and-tuck mechanism, or pull-and-lock mechanism as described with reference to FIGS. 3A-3C.

Figure 15A:
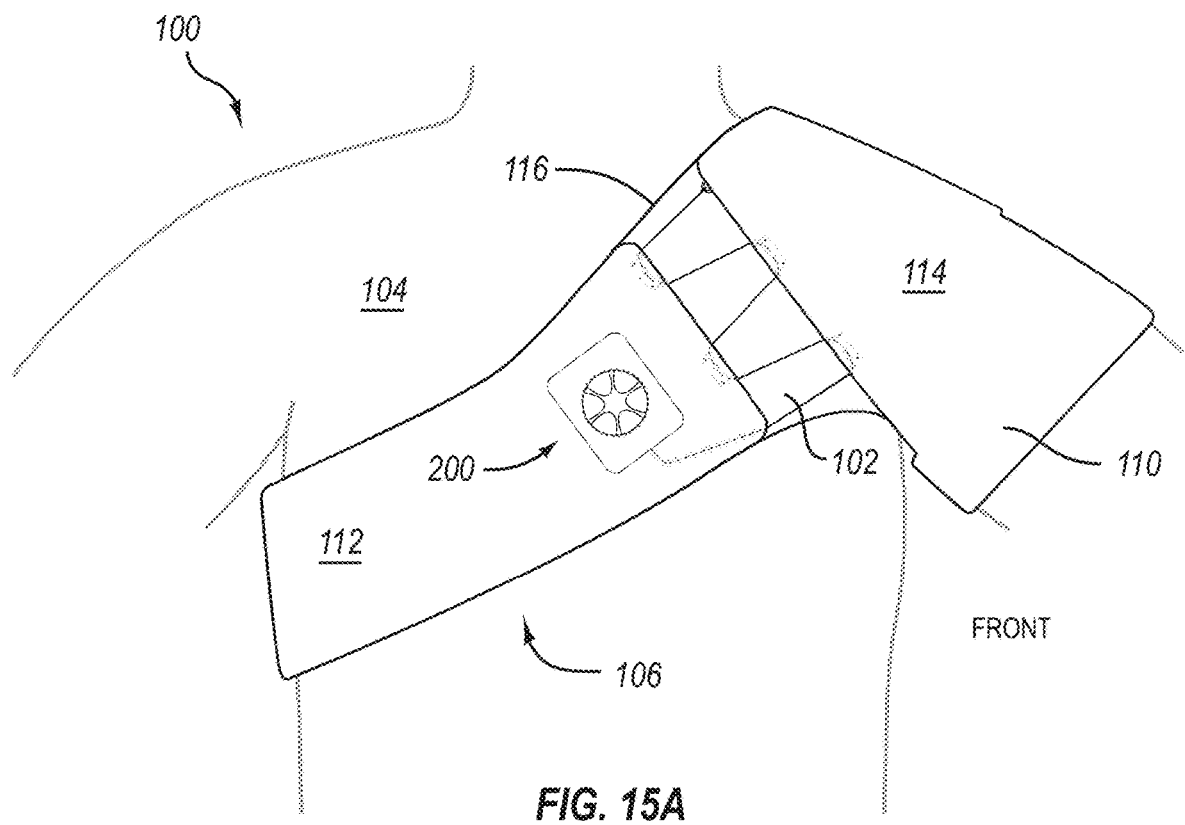
FIGS. 15A and 15B illustrate an example cryotherapy system of FIGS. 1A-1D configured to fit a shoulder.
Figure 15B:
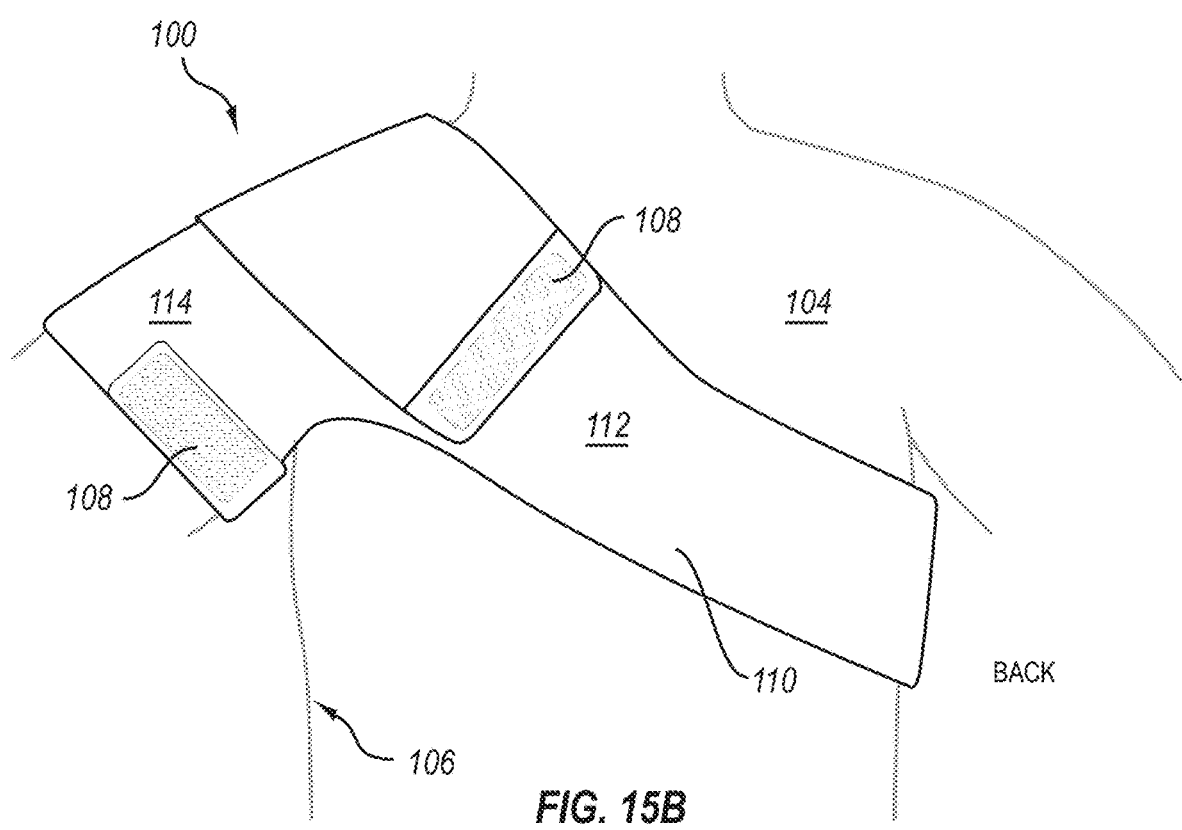

FIGS. 15A and 15B illustrate an example cryotherapy system 100 of FIGS. 1A-1D configured to fit a shoulder of the user 104. Specifically, FIG. 15A is a front view of the cryotherapy system 100 and FIG. 15B is a rear view of the cryotherapy system 100. As illustrated in FIGS. 15A and 15B, when configured to fit a shoulder, the securing mechanism 108 may be split to secure the cryotherapy system 100 around an arm of the user 104 and under an opposite shoulder of the user 104. The tightening mechanism 200 may then apply external pressure to the shoulder of the user 104.

When the cryotherapy system 100 is configured to fit a shoulder, the cold pack (not shown), the inner layer 102, the outer layer 110, etc. may take shapes to conform to the shape of the shoulder. The cryotherapy system 100 configured to fit a shoulder may include foam pads as described in FIGS. 5A-6B, may omit the securing mechanism 108, may implement alternative securing mechanisms 108 described with reference to FIGS. 8A-8C, may include a cold therapy water circulation system as described with reference to FIGS. 7A and 7B, or any combination thereof. Additionally or alternatively, the tightening mechanism 200 may include jam cleat, wind-and-tuck mechanism, or pull-and-lock mechanism as described with reference to FIGS. 3A-3C.

Figure 16A:
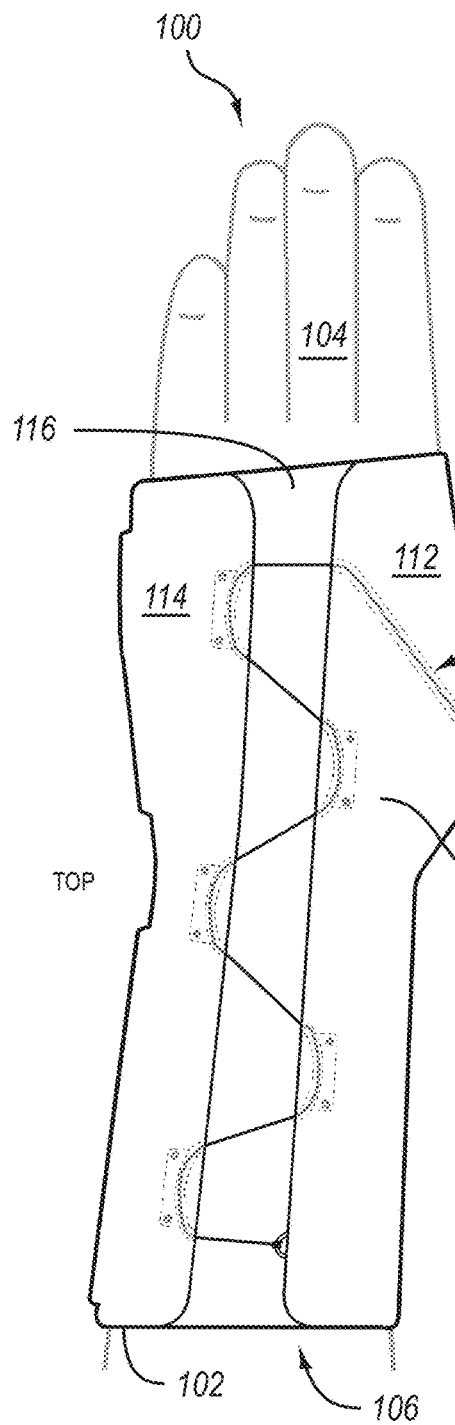
FIGS. 16A and 16B illustrate an example cryotherapy system of FIGS. 1A-1D configured to fit a wrist.
Figure 16B:
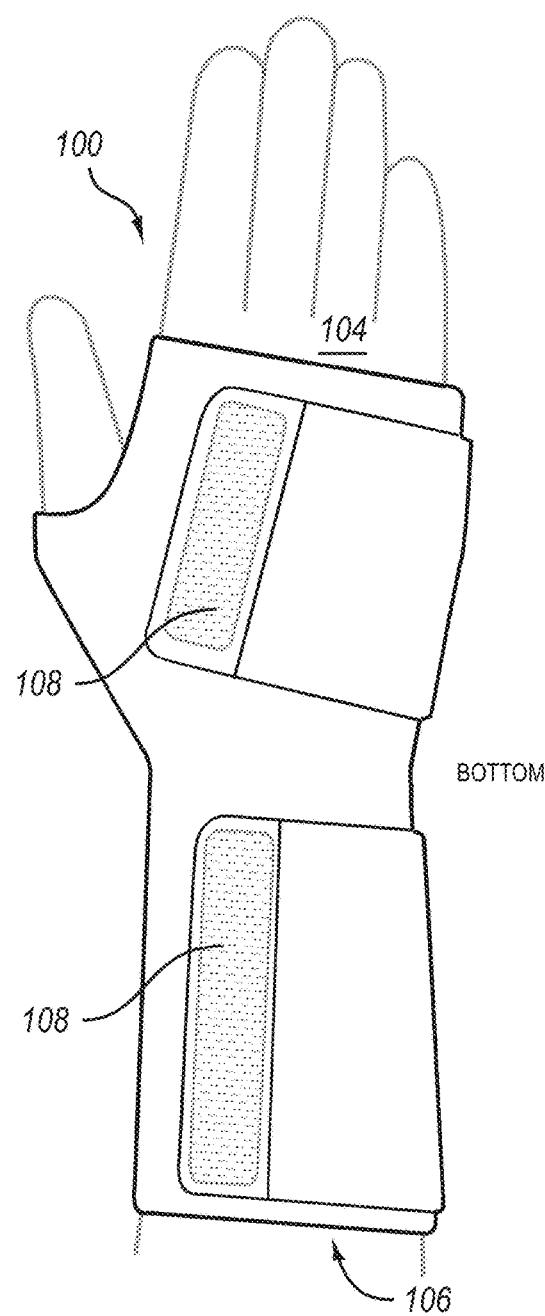

FIGS. 16A and 16B illustrate an example cryotherapy system 100 of FIGS. 1A-1D configured to fit a wrist of the user 104. Specifically, FIG. 16A is a top view of the cryotherapy system 100 and FIG. 16B is a bottom view of the cryotherapy system 100. As illustrated in FIGS. 16A and 16B, when configured to fit a wrist, the securing mechanism 108 may be split to secure the cryotherapy system 100 around a wrist of the user 104. The tightening mechanism 200 may then apply external pressure to the wrist of the user 104.

When the cryotherapy system 100 is configured to fit a wrist, the cold pack (not shown), the inner layer 102, the outer layer 110, etc. may take shapes to conform to the shape of the wrist. The cryotherapy system 100 configured to fit a wrist may include foam pads as described in FIGS. 5A-6B, may omit the securing mechanism 108, may implement alternative securing mechanisms 108 described with reference to FIGS. 8A-8C, may include a cold therapy water circulation system as described with reference to FIGS. 7A and 7B, or any combination thereof. Additionally or alternatively, the tightening mechanism 200 may include jam cleat, wind-and-tuck mechanism, or pull-and-lock mechanism as described with reference to FIGS. 3A-3C

Figure 17A:
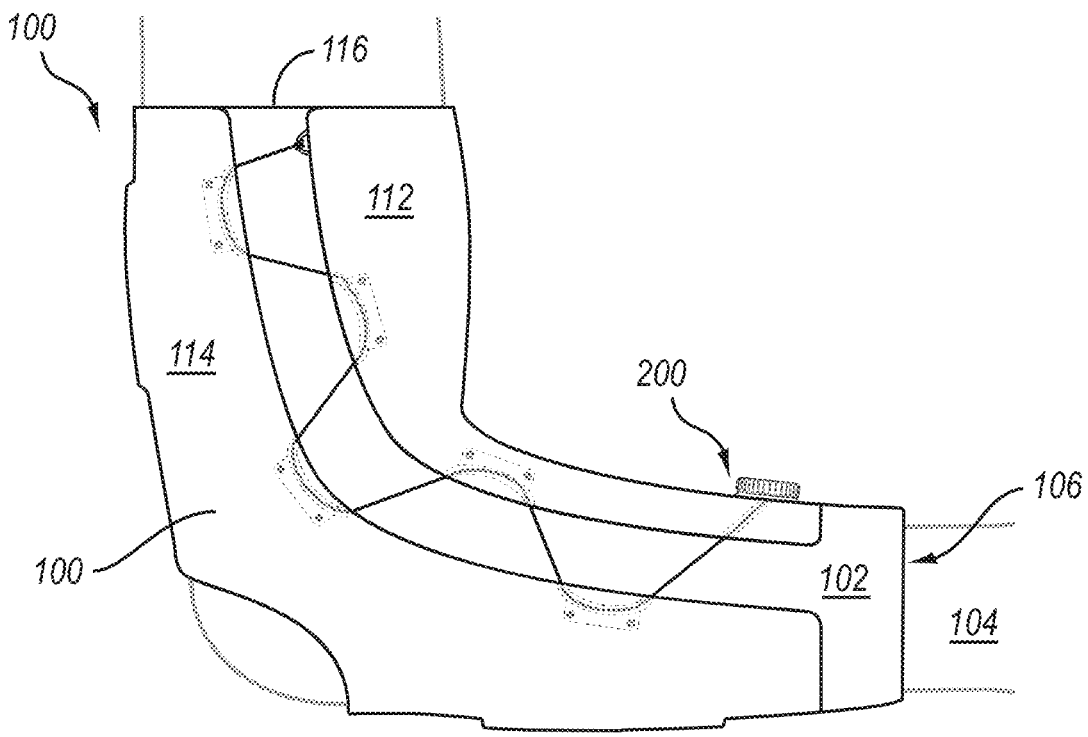
FIGS. 17A and 17B illustrate an example cryotherapy system of FIGS. 1A-1D configured to fit an elbow.
Figure 17B:
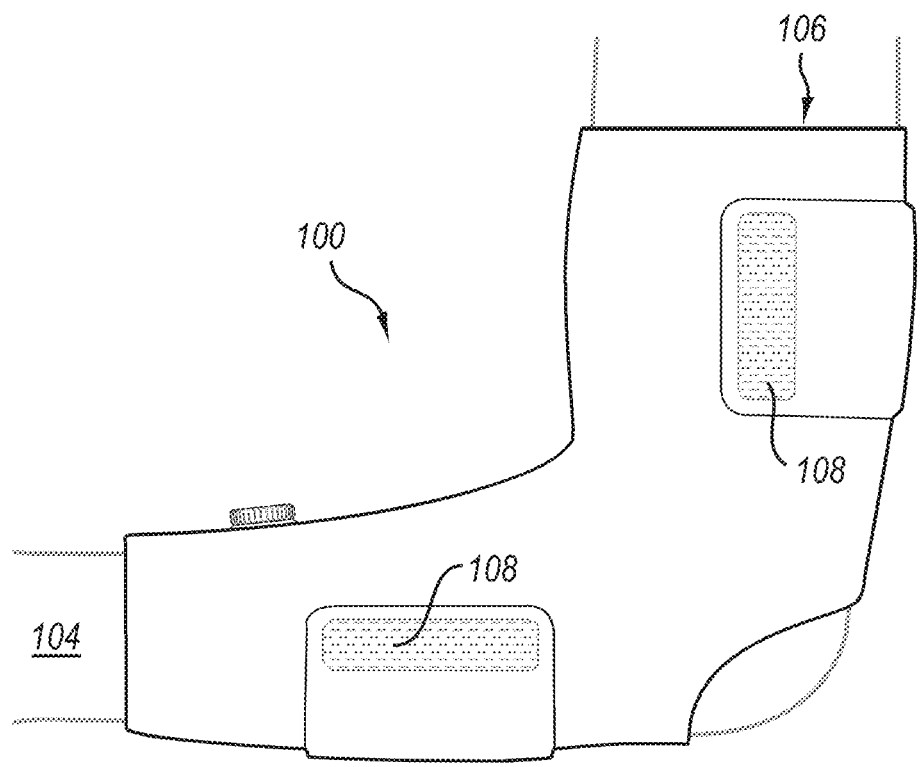

FIGS. 17A and 17B illustrate an example cryotherapy system 100 of FIGS. 1A-1D configured to fit an elbow of the user 104. Specifically, FIG. 17A is a first side view of the cryotherapy system 100 and FIG. 17B is a second side view of the cryotherapy system 100. As illustrated in FIGS. 17A and 17B, when configured to fit an elbow, the securing mechanism 108 may be split to secure the cryotherapy system 100 around an arm of the user 104. The tightening mechanism 200 may then apply external pressure to the elbow of the user 104.

When the cryotherapy system 100 is configured to fit an elbow, the cold pack (not shown), the inner layer 102, the outer layer 110, etc. may take shapes to conform to the shape of the elbow. The cryotherapy system 100 configured to fit an elbow may include foam pads as described in FIGS. 5A-6B, may omit the securing mechanism 108, may implement alternative securing mechanisms 108 described with reference to FIGS. 8A-8C, may include a cold therapy water circulation system as described with reference to FIGS. 7A and 7B, or any combination thereof. Additionally or alternatively, the tightening mechanism 200 may include jam cleat, wind-and-tuck mechanism, or pull-and-lock mechanism as described with reference to FIGS. 3A-3C.

Figure 18A:
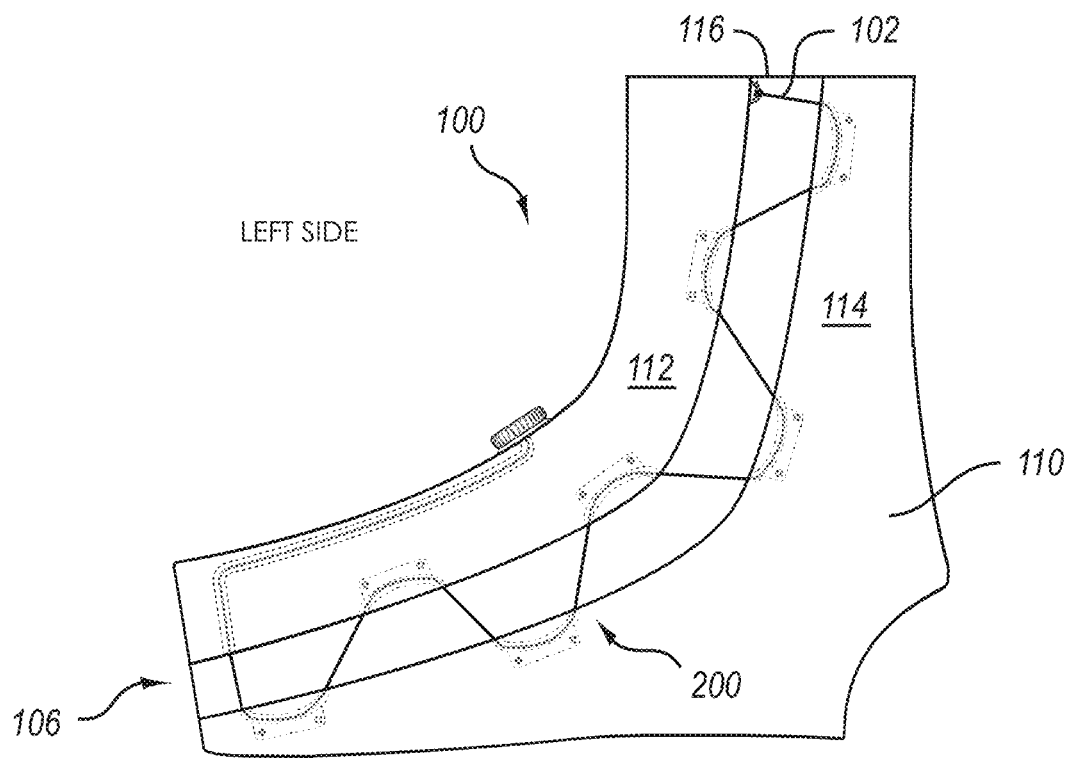
FIGS. 18A and 18B illustrate an example cryotherapy system of FIGS. 1A-1D configured to fit an ankle-foot combination.
Figure 18B:
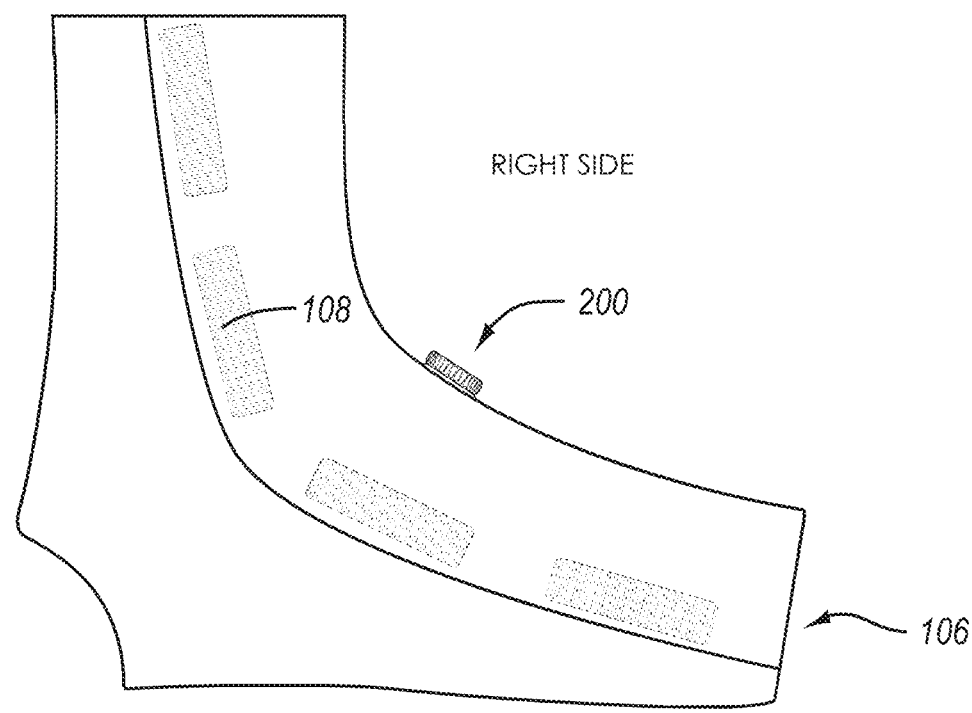

FIGS. 18A and 18B illustrate an example cryotherapy system 100 of FIGS. 1A-1D configured to fit an ankle-foot combination. Specifically, FIG. 18A is a first side view of the cryotherapy system 100 and FIG. 18B is a second side view of the cryotherapy system 100. As illustrated in FIGS. 18A and 18B, when configured to fit an ankle-foot combination, the securing mechanism 108 may be positioned along a first side to secure the cryotherapy system 100 around the ankle and foot of the user. The tightening mechanism 200 may then apply external pressure to the ankle-foot combination of the user.

When the cryotherapy system 100 is configured to fit an ankle-foot combination, the cold pack (not shown), the inner layer 102, the outer layer 110, etc. may take shapes to conform to the shape of the ankle-foot combination. The cryotherapy system 100 configured to fit an ankle-foot combination may include foam pads as described in FIGS. 5A-6B, may omit the securing mechanism 108, may implement alternative securing mechanisms 108 described with reference to FIGS. 8A-8C, may include a cold therapy water circulation system as described with reference to FIGS. 7A and 7B, or any combination thereof. Additionally or alternatively, the tightening mechanism 200 may include jam cleat, wind-and-tuck mechanism, or pull-and-lock mechanism as described with reference to FIGS. 3A-3C

Figure 19A:
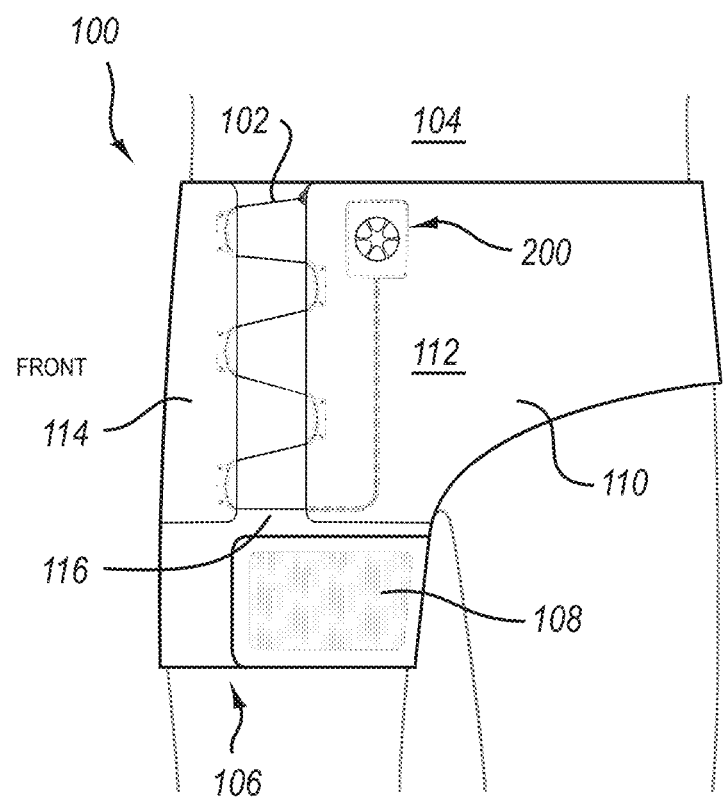
FIGS. 19A and 19B illustrate an example cryotherapy system of FIGS. 1A-1D configured to fit a hip.
Figure 19B:
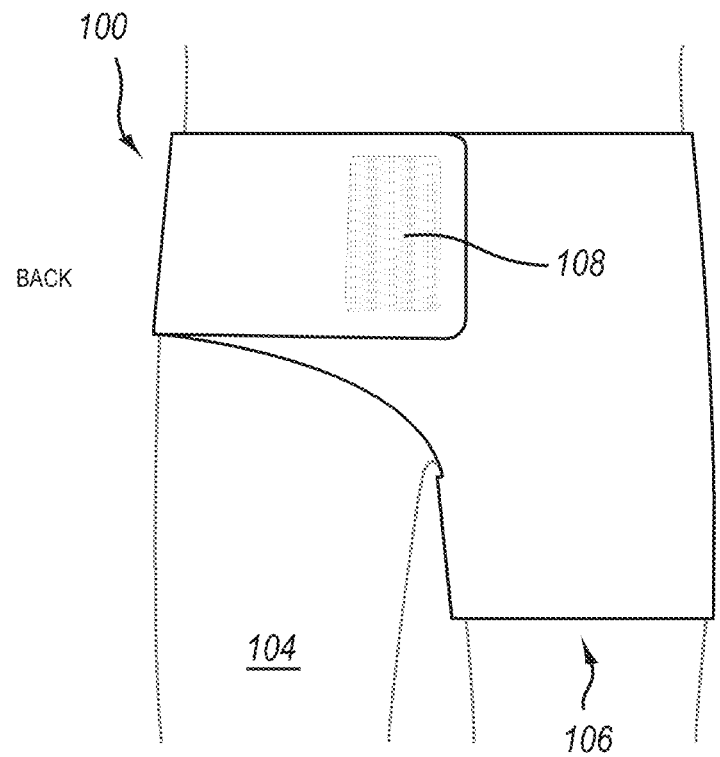

FIGS. 19A and 19B illustrate an example cryotherapy system 100 of FIGS. 1A-1D configured to fit a hip of the user 104. Specifically, FIG. 19A is a front view of the cryotherapy system 100 and FIG. 19B is a rear view of the cryotherapy system 100. As illustrated in FIGS. 19A and 19B, when configured to fit a hip, the securing mechanism 108 may be split to secure the cryotherapy system 100 around a leg of the user 104 and around a waist of the user 104. The tightening mechanism 200 may then apply external pressure to the hip of the user 104.

When the cryotherapy system 100 is configured to fit a hip, the cold pack (not shown), the inner layer 102, the outer layer 110, etc. may take shapes to conform to the shape of the hip. The cryotherapy system 100 configured to fit a hip may include foam pads as described in FIGS. 5A-6B, may omit the securing mechanism 108, may implement alternative securing mechanisms 108 described with reference to FIGS. 8A-8C, may include a cold therapy water circulation system as described with reference to FIGS. 7A and 7B, or any combination thereof. Additionally or alternatively, the tightening mechanism 200 may include jam cleat, wind-and-tuck mechanism, or pull-and-lock mechanism as described with reference to FIGS. 3A-3C.

As noted elsewhere herein, embodiments of the invention can be configured for specificity to any portion, or portions, of the anatomy of a user. Thus, it will be appreciated that multiple devices, one example of which is the cryotherapy system 100, can be removably attached together to provide a customized configuration. The devices can be attached together using mechanisms such as zippers, hook-and-loop type closures, and/or any other securing device that permits removable attachment of the devices to each other, including the example securing devices disclosed herein.

Figure 20:
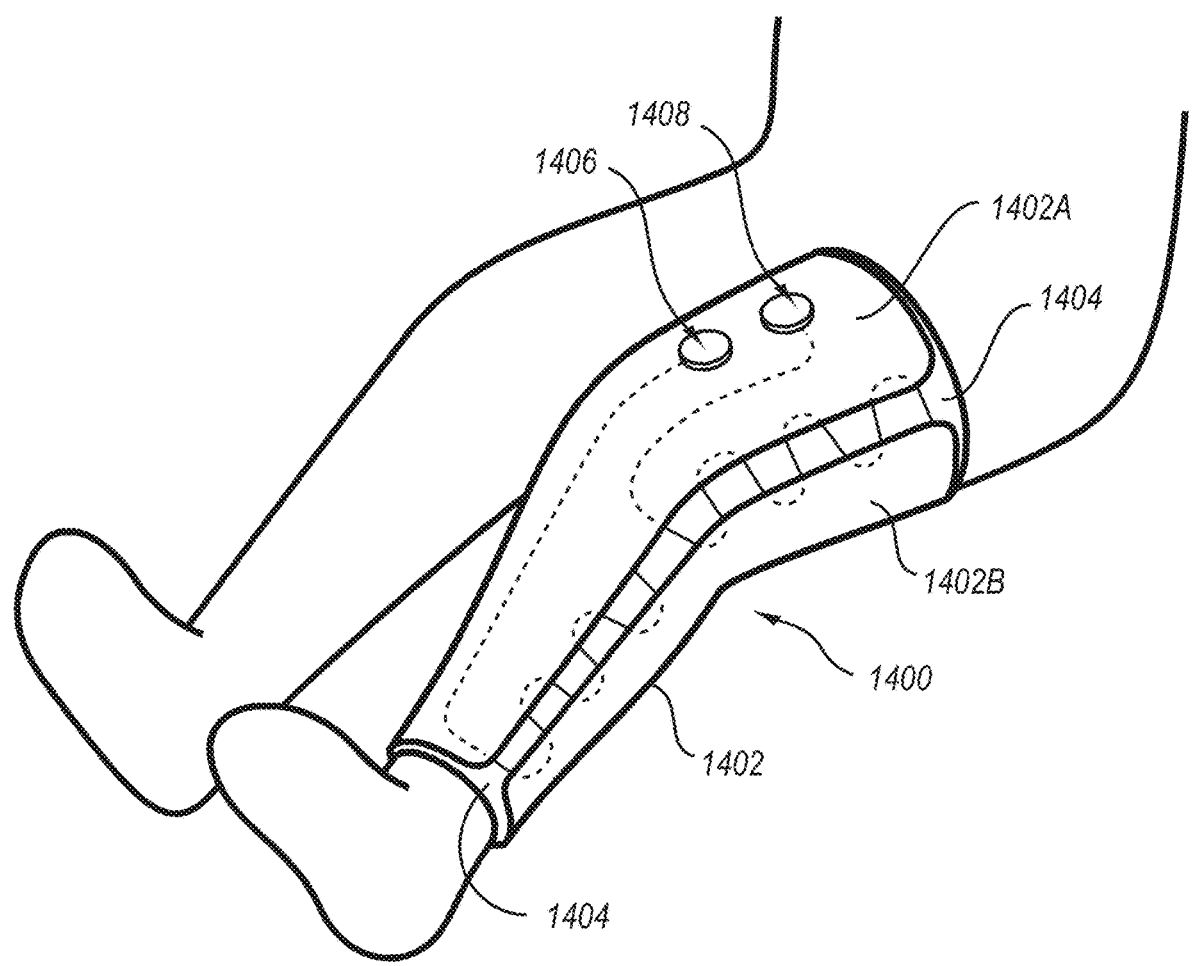
FIG. 20 illustrates an example of a thigh-to-ankle cryotherapy system.

With attention now to FIG. 20, details are provided concerning a thigh-to-ankle cryotherapy system, one embodiment of which is denoted at 1400. Except as noted below, the thigh-to-ankle cryotherapy system 1400 may be similar, or even identical, in construction and operation to any of the other embodiments disclosed herein.

As noted above, embodiments of the invention can be configured to fit any portion, or portions, of the anatomy of a user. Similar to other embodiments disclosed herein, the thigh-to-ankle cryotherapy system 1400 optionally includes one or more thermal packs (not shown in FIG. 20), examples of which are disclosed herein.

As well, the thigh-to-ankle cryotherapy system 1400 may include an outer layer 1402 having portions 1402A and 1402B, one or both of which are movable relative to each other and to an inner layer 1404. As disclosed elsewhere herein, the inner layer 1404 may be omitted in some embodiments. Moreover, the inner layer 1404, when present, and outer layer 1406 may be constructed in the same manner and with the same materials as disclosed in any of the other embodiments of layers disclosed herein.

With continued reference to FIG. 20, the thigh-to-ankle cryotherapy system 1400 includes one or more tightening systems, such as tightening systems 1406 and 1408 for example. The tightening systems 1406 and 1408 may be similar, or identical, to each other, but that is not required. The tightening systems 1406 and 1408 can be any of the example tightening systems disclosed herein. In the particular example of FIG. 20, the tightening system 1406 is configured and arranged to tighten a lower portion of the outer layer 1402, while the tightening system 1408 is configured and arranged to tighten an upper portion of the outer layer 1402. From a therapeutic perspective, at least, it may be advantageous to first tighten the lower portion of the outer layer 1402, and subsequently tighten the upper portion of the outer layer 1402. Moreover, the use of a plurality of tightening systems in this embodiment lends a high degree of customization to the user/therapist in terms of the amount of compression applied to different parts of the anatomy of the user. In fact, some embodiments may include more than two tightening systems, while other embodiments employ only a single tightening system. Finally, while the example of FIG. 20 indicates that the tightening systems 1404 and 1406 are operable from a location near an upper thigh of the user, it should be understood that the tightening systems 1404 and 1406 can be configured to be operated from other locations as well, and the scope of the invention is not limited to the particular arrangement depicted in FIG. 20.

Figure 21:
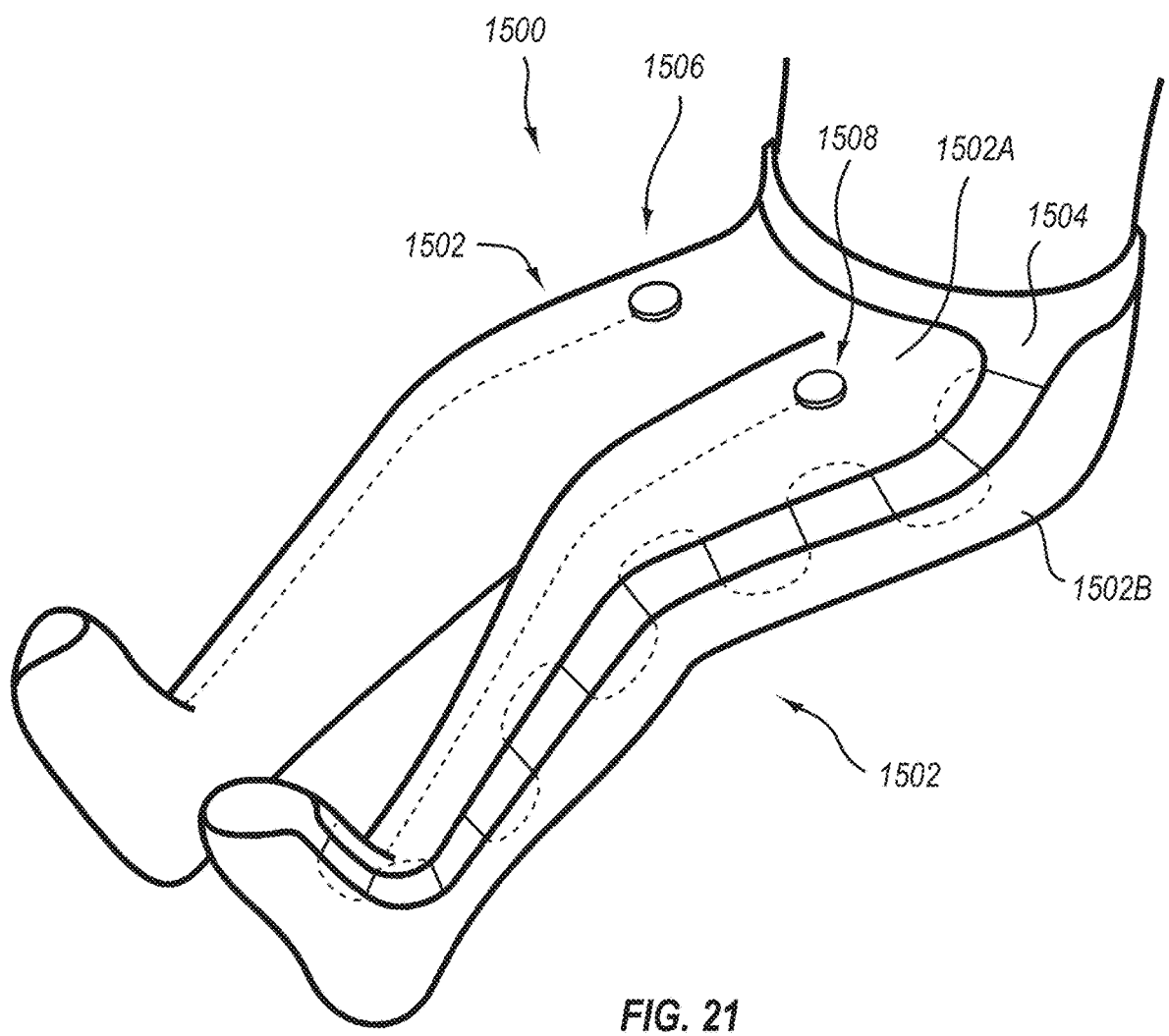
FIG. 21 illustrates an example of a cryotherapy garment.

Turning finally to FIG. 21, details are provided concerning a cryotherapy garment, an example of which is denoted at 1500. Except as noted below, the cryotherapy garment 1500 may be similar, or even identical, in construction and operation to any of the other embodiments disclosed herein.

In the example of FIG. 21, the cryotherapy garment 1500 is generally in the form of a pair of pants that a user can wear over bare skin, or over clothing, although the cryotherapy garment 1500 could take other forms as well, such as a shirt or portion thereof, or a garment that fits around the trunk of a user, possibly in the form of a vest for example. The cryotherapy garment 1500 has a wide range of applications and may, for example, be particularly useful to endurance athletes such as runners, skiers or cyclists for example, after having competed in an event lasting several hours or more. However, the cryotherapy garment 1500 can be used by other types of users, as well in a variety of therapeutic applications. The example cryotherapy garment 1500, like the other embodiments disclosed herein, may be easier to use and more effective than inflatable devices, and may also enable a much higher degree of mobility to the user.

As well, the cryotherapy garment 1500 may include an outer layer 1502 having portions 1502A and 1502B, one or both of which are movable relative to each other and to an inner layer 1504. The movable portion(s) of the layers on one leg may optionally be attached to the movable portion(s) of the layers on the other leg. For example, the outer layer 1502 may have a total of only two pieces of material, one on the front of the legs of the user and one on the back of the legs of the user. In an alternative embodiment, the outer layer 1502 may have a total of four different pieces of material, one each on the front of each leg and one each on the back of each leg. The front pieces in this example are not attached to each other, nor are the back pieces attached to each other. More generally, the cryotherapy garment 1500, like the other embodiments disclosed herein, can be constructed with any number of different pieces of material. A relatively greater number of layer pieces and/or tightening mechanisms may enable, for example, a relatively high level of customization of the amount of compression that is applied to various parts of the anatomy of the user. It should be noted that an inner layer 1504, if present, can be constructed in any of the aforementioned configurations discussed in connection with the outer layer 1506.

As disclosed elsewhere herein, the inner layer 1504 may be omitted in some embodiments. Moreover, the inner layer 1504, if present, and outer layer 1502 may be constructed in the same manner and with the same materials as disclosed in any of the other embodiments of layers disclosed herein.

With continued reference to FIG. 21, the cryotherapy garment 1500 may include first and second tightening systems 1506 and 1508, respectively disposed on a leg portion of the cryotherapy garment 1500. With this configuration, a user is able to impose a level of compression on one leg that is different from a level of compression imposed on the other leg, or a user can apply about the same level of compression to both legs. It should be noted that while the example cryotherapy garment 1500 includes a single tightening system on each leg, each of the legs could alternatively be configured with two or more tightening systems, in a configuration which could be similar to that disclosed in FIG. 20, for example. The tightening systems 1506 and 1508 may be configured and arranged to be operated from respective locations on the upper thighs of the user, or any other desired location. Finally, the example of FIG. 21 indicates an arrangement where the tightening systems 1506 and 1508 tighten the outer layer 1502 first from a distal location, namely, near the feet or ankles of a user, and subsequently toward a proximal location, namely, near an upper thigh of waist of a user. Applying compression in this order may provide desirable therapeutic effects, though it should be understood that one or more of the tightening systems 1506 and 1508 can be configured and arranged to provide sequential compression in other directions and orders as well.

As in the case of the other embodiments disclosed herein, the cryotherapy garment 1500 may include one or more thermal packs and/or other therapeutic devices. These devices, as is the case with other embodiments disclosed herein, can be configured and arranged to suit the general, and specific, anatomy of a user. As an example of the former, it may not be necessary or desired to include such a device on all portions of the inside front portions of the lower legs since much of that area is bone rather than muscle. However, therapeutic devices could be included in these areas if desired.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

It should be appreciated with the benefit of this disclosure and the numerous example embodiments described herein, the cryotherapy systems (e.g., 100, 600, 900, 1000, and 1100) may include one or more components, features, systems, etc. as described above in any combination. Thus, a particular configuration may include one or more components not explicitly shown together without limitation.

As will be apparent from the disclosure, one or more embodiments of the invention, such as the cryotherapy system 100 for example, can provide one or more advantageous and unexpected effects, in any combination, some examples of which are set forth below. It should be noted that such effects enumerated herein are neither intended, nor should be construed, to limit the scope of the claimed invention in any way.

By way of illustration, one or more embodiments of the invention may be advantageous inasmuch as they enable a user to combine cold therapy and compression in a single easily portable device.

As well, one or more embodiments may be advantageous in that they combine cold therapy and compression capabilities in a single device that is lightweight and portable and requires no external support systems or components.

Further, one or more embodiments of the device may be advantageous in that they can enable a user to quickly and easily adjust a compressive force exerted by the device on an injured, or otherwise affected, portion of the anatomy of the user, and such adjustments can be made without having to reposition the device on the anatomy of the user.

Additionally, one or more embodiments of the invention may be advantageous relative to inflatable devices that are sometimes used to apply compression to an affected portion of the anatomy of a user, in that such embodiments effect compression, and release of compression, by employing relative translational motion between elements of the device, while inflatable devices typically rely on concentric elements that do not change position relative to each other in use, or preparatory to use. Correspondingly, one or more embodiments of the invention become relatively smaller in circumference as increased compression is applied, while inflatable devices, by their nature, necessarily increase in circumference as increased compression, effected by greater inflation, is applied. The relatively smaller profile of such embodiments of the invention may enable, among other things, enhanced mobility of the user.

As well, and disclosed herein, a single embodiment of the invention can exert compressive forces of varying magnitude on different portions of the anatomy of a user. In contrast, inflatable devices typically lack this capability since the air pressure is the same everywhere in the inflatable device.

Further, the compressive force imposed by an embodiment of the invention is easily adjusted to increase, or decrease, in magnitude. In contrast, an inflatable device can be adjusted to reduce an imposed compressive force by releasing air or another gas from the inflatable device. However, once such an adjustment is made, it may be inconvenient, difficult, or impossible to re-inflate the device in order to increase the magnitude of an exerted compressive force.

Embodiments disclosed herein may also be advantageous in that they do not require an inflation device or inflatable bladder. Inflation devices may be unreliable and may require a significant amount of time to effect inflation of a bladder. As well, any inflatable item is susceptible to punctures that can render it non-functional.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A therapy system, comprising:
   an inner layer having an inner surface and an outer surface;
   an outer layer whose overall length is adjustable, the outer layer including first and second portions that are not part of, but are attached to, the inner layer, wherein an end of the first portion is completely separable from an end of the second portion so as to define a separation that takes the form of a gap in a material of the outer layer and wherein the gap is spanned by a spanning material, and wherein the outer layer includes a first free end and second free end that are releasably attachable to each other;
   a therapeutic device removably positioned so that the inner surface of the inner layer is disposed between the therapeutic device and an extremity of a user when the extremity is positioned in an opening defined by the inner layer; and
   an adjustable and manually operable tightening mechanism comprising a lace connected to the first and second portions of the outer layer and the lace is engaged with a mechanical lace tensioner that is operable to change, by either drawing the first and second portions toward each other or by allowing the first and second portions to move away from each other, a magnitude of a compressive force exerted by the outer layer on the extremity when the extremity is positioned within the opening defined by the inner layer, wherein the tightening mechanism is further operable to translate part of one of the first and second portions of the outer layer relative to the inner layer so as to vary a width of the gap.

2. The therapy system as recited in claim 1, wherein the therapeutic device comprises one of a cold pack, a heat pack, or a water circulation pad.

3. The therapy system of claim 1, wherein the adjustable and manually operable tightening mechanism further comprises:
   a first lace retainer attached to the first portion of the outer layer, wherein the lace is routed through the first lace retainer;
   a second lace retainer attached to the second portion of the outer layer, wherein the lace is routed through the second lace retainer; and
   the mechanical lace tensioner is configured to apply tension to the lace and to retract the lace, so as to move one of the lace retainers relative to the other of the lace retainers.

4. The therapy system as recited in claim 1, further comprising a foam pad disposed between the inner layer and the therapeutic device, wherein the foam pad has first and second portions with different respective thicknesses.

5. The therapy system as recited in claim 1, wherein the spanning material comprises either a portion of the inner layer, or a portion of the outer layer.

6. The therapy system of claim 1, wherein the adjustable and manually operable tightening mechanism maintains the first and second portions of the outer layer in position relative to each other after a position of one of the first and second portions relative to the other of the first and second portions has been changed.

7. The therapy system of claim 1, wherein the adjustable and manually operable tightening mechanism facilitates thermal communication between the therapeutic device and the extremity of the user when the extremity is positioned within the opening defined by the inner layer.

8. The therapy system as recited in claim 1, wherein the therapy system is configured to fit one or more of an ankle-foot combination of a user, a shoulder of a user, a wrist of a user, an elbow of a user, a calf of a user, a foot-to-hip of a user, an ankle-to-hip of a user, or a hip of a user.

9. The therapy system as recited in claim 1, wherein the therapeutic device is a single cold pack having a length such that the cold pack encloses a majority of the extremity of the user when the extremity is positioned in the opening defined by the inner layer.

10. The therapy system as recited in claim 1, wherein the therapeutic device is a single cold pack that extends along a majority of a length of the inner layer.

11. The therapy system as recited in claim 1, wherein the adjustable and manually operable tightening mechanism is configured, and operable, to apply different levels of compression at different respective locations on the extremity of the user when the extremity is positioned in the opening defined by the inner layer.

12. The therapy system as recited in claim 1, wherein the first free end and the second free end are releasably attachable to each other by way of a securing mechanism configured and arranged to enable releasable attachment of the first portion to the second portion by overlapping of the first portion with the second portion.

13. The therapy system as recited in claim 1, wherein the therapy device is a cold pack that comprises one of a reusable self-contained chemical cold compress, a thermodynamic gel, a bag configured to hold a volume of liquid and/or solid, or a portion of a cold therapy water circulation system.

* * * * *